(12) United States Patent
Davidovits et al.

(10) Patent No.: US 11,619,634 B2
(45) Date of Patent: Apr. 4, 2023

(54) METHODS OF DIAGNOSING AND TREATING LUNG CANCER

(71) Applicants: Savicell Diagnostic Ltd., Haifa (IL); Ramot at Tel-Aviv University Ltd., Tel-Aviv (IL)

(72) Inventors: Giora Davidovits, Haifa (IL); Fernando Patolsky, Tel Aviv (IL); David Eyal Davidovits, Haifa (IL); Irit Arbel, Haifa (IL); Shoval Tirman, Haifa (IL); Aviv Lutaty, Haifa (IL); Tali Scienmann, Haifa (IL); Reuven Tirosh, Tel Aviv (IL); Hagit Peretz-Soroka, Tel Aviv (IL)

(73) Assignees: Savicell Diagnostic Ltd., Haifa (IL); Ramot at Tel-Aviv University Ltd., Tel-Aviv (IL)

( * ) Notice: Subject to any disclaimer, the term of this patent is extended or adjusted under 35 U.S.C. 154(b) by 215 days.

(21) Appl. No.: 16/640,392

(22) PCT Filed: Aug. 20, 2018

(86) PCT No.: PCT/IL2018/050920
§ 371 (c)(1),
(2) Date: Feb. 20, 2020

(87) PCT Pub. No.: WO2019/038761
PCT Pub. Date: Feb. 28, 2019

(65) Prior Publication Data
US 2020/0355689 A1 Nov. 12, 2020

Related U.S. Application Data

(60) Provisional application No. 62/547,906, filed on Aug. 21, 2017.

(51) Int. Cl.
*G01N 33/574* (2006.01)
*G01N 33/50* (2006.01)
*A61K 45/06* (2006.01)

(52) U.S. Cl.
CPC .............. *G01N 33/57423* (2013.01); *G01N 33/5091* (2013.01); *A61K 45/06* (2013.01)

(58) Field of Classification Search
CPC ......... G01N 33/57423; G01N 33/5091; G01N 33/57484; A61K 45/06
See application file for complete search history.

(56) References Cited

U.S. PATENT DOCUMENTS

| 6,451,316 | B1 | 9/2002 | Srivastava |
| 2006/0142546 | A1 | 6/2006 | Hanisch |
| 2009/0305319 | A1 | 12/2009 | Baudenbacher et al. |
| 2011/0059861 | A1 | 3/2011 | Nolan et al. |
| 2013/0224789 | A1 | 8/2013 | Tirosh et al. |
| 2014/0255972 | A1 | 9/2014 | Tirosh et al. |
| 2017/0003306 | A1 | 1/2017 | Scoles et al. |
| 2018/0038849 | A1 | 2/2018 | Tirosh et al. |

FOREIGN PATENT DOCUMENTS

| CN | 101213455 | 7/2008 |
| EP | 1736780 | 12/2006 |
| JP | 2006-132989 | 5/2006 |
| JP | 2013-521763 | 6/2013 |
| JP | 2014-512006 | 5/2014 |
| JP | 2017-502312 | 1/2017 |
| WO | WO 2008/018905 | 2/2008 |
| WO | WO 2010/107116 | 9/2010 |
| WO | WO 2011/000572 | 1/2011 |
| WO | WO 2011/100483 | 8/2011 |
| WO | WO 2012/137207 | 10/2012 |
| WO | WO 2015/092726 | 6/2015 |
| WO | WO 2019/038761 | 2/2019 |

OTHER PUBLICATIONS

International Search Report and the Written Opinion dated Nov. 12, 2018 From the International Searching Authority Re. Application No. PCT/IL2018/050920. (13 Pages).
Advisory Action Before the Filing of An Appeal Brief dated Apr. 6, 2017 From the US Patent and Trademark Office Re. U.S. Appl. No. 14/280,612. (4 pages).
Applicant-Initiated Interview Summary dated May 23, 2017 From the US Patent and Trademark Office Re. U.S. Appl. No. 14/280,612. (4 pages).
Communication Pursuant to Article 94(3) EPC dated Feb. 3, 2015 From the European Patent Office Re. Application No. 12721945.9.
Communication Pursuant to Article 94(3) EPC dated Nov. 6, 2015 From the European Patent Office Re. Application No. 12721945.9.
Examination Report Under Sections 12 & 13 of the Patents Act, 1970 and the Patents Rules, 2003 dated Jul. 11, 2018 From the Government of India, Intellectual Property India, Patents, Designs, Trade Marks, Geographical Indications Re. Application No. 1761/MUMNP/2013. (5 Pages).
Examiner-Initiated Interview Summary dated Jul. 12, 2016 From the US Patent and Trademark Office Re. U.S. Appl. No. 14/280,612.
Examiner-Initiated Interview Summary dated Oct. 18, 2016 From the US Patent and Trademark Office Re. U.S. Appl. No. 14/280,612.
International Preliminary Report on Patentability dated Mar. 5, 2020 From the International Bureau of WIPO Re. Application No. PCT/IL2018/050920. (9 Pages).

(Continued)

*Primary Examiner* — Changhwa J Cheu

(57) ABSTRACT

A method of diagnosing lung cancer in a subject-in-need thereof is provided. The method comprises:
(a) providing a biological sample of the subject which comprises peripheral blood mononuclear cells (PBMCs);
(b) in vitro contacting the PBMCs with a stimulant selected from the group consisting of the stimulants listed in Tables 3 and 4; and
(c) measuring metabolic activity of the PBMCs having been contacted according to (b), wherein a statistically significant change in the metabolic activity of the PBMCs as compared to a control sample is indicative of lung cancer.

17 Claims, 6 Drawing Sheets

Specification includes a Sequence Listing.

(56) References Cited

OTHER PUBLICATIONS

International Preliminary Report on Patentability dated Oct. 17, 2013 From the International Bureau of WIPO Re. Application No. PCT/IL2012/050125.
International Search Report and the Written Opinion dated Sep. 6, 2012 From the International Searching Authority Re. Application No. PCT/IL2012/050125.
Notice of Reason for Rejection dated Dec. 4, 2015 From the Japanese Patent Office Re. Application No. 2014-503276 and Its Translation Into English.
Notice of the Reason for Rejection dated Jun. 26, 2018 From the Korean Intellectual Property Office Re. Application No. 10-2013-7027588. (9 Pages).
Office Action dated Sep. 4, 2014 From The State Intellectual Property Office of the People's Republic of China Re. Application No. 201280022396.9 and Its Translation Into English.
Office Action dated May 14, 2015 From The State Intellectual Property Office of the People's Republic of China Re. Application No. 201280022396.9 and Its Summary in English.
Official Action dated Aug. 1, 2013 From the US Patent and Trademark Office Re. U.S. Appl. No. 13/817,543.
Official Action dated Sep. 9, 2019 From the US Patent and Trademark Office Re. U.S. Appl. No. 151724,299. (13 pages).
Official Action dated Jun. 16, 2016 From the US Patent and Trademark Office Re. U.S. Appl. No. 14/280,612.
Official Action dated Jun. 21, 2016 From the US Patent and Trademark Office Re. U.S. Appl. No. 14/280,612.
Official Action dated Oct. 21, 2016 From the US Patent and Trademark Office Re. U.S. Appl. No. 14/280,612.
Patent Examination Report dated Mar. 18, 2016 From the Australian Government, IP Australia Re. Application No. 2012240953.
Search Report dated Sep. 4, 2014 From The State Intellectual Property Office of the People's Republic of China Re. Application No. 201280022396.9 and Its Translation Into English.
Translation of Notice of the Reason for Rejection dated Jun. 26, 2018 From the Korean Intellectual Property Office Re. Application No. 10-2013-7027588. (8 Pages).
Hartung et al. "Flow Cytometric Analysis of BCL-2 Can Distinguish Small Numbers of Acute Lymphoblastic Leukaemia Cells From B-Cell Precursors", British Journal of Haematology, 127: 50-58, 2004.
Henning et al. "Relevance of Tumor Microenvironment for Progression, Therapy and Drug Development", Anti-Cancer Drugs, XP009162065, 15(1): Jan. 7-14, 2004.
Huang et al. "Gene Expression Analysis With An Integrated CMOS Microarray by Time-Resolved Fluorescence Detection", Biosensors & Bioelectronics, 26(5): 2660-2665, Jan. 15, 2011.
Hynes et al. "In Vitro Analysis of Cell Metabolism Using A Long-Decay pH-Sensitive Lanthanide Probe and Extracellular Acidification Assay", Analytical Biochemistry, XP026130719, 390(1): 21-28, Jul. 1, 2009.
Naume et al. "Detection of Isolated Tumor Cells in Peripheral Blood and in BM: Evaluation of A New Enrichment Method", Cytotherapy, 6(3): 244-252, 2004.
Oertel et al. "Immunocytochemical Methods in Haematology and Oncology", Journal of Cancer Research and Clinical Oncology, 126(8): 425-440, Aug. 2000.
Otto et al. "Microphysiological Testing for Chemosensitivity of Living Tumor Cells With Multiparametric Microsensor Chips", Cancer Detection and Prevention, XP002682126, 27(4): 291-296, 2003.
Sprague et al. "Multiparametric Sensor-Chip Based Technology for Monitoring Metabolic Activity: A Proof-of-Principle Study With Live Tissue", Clinical Laboratory, XP009162068, 52(7-8): 375-384, 2006.
Wong et al. "Detection of Circulating Tumour Cells and Nodal Metastasis by Reverse Transcriptase-Polvmerase Chain Reaction Technique", British Journal of Surgery, 84(6): 834-839, Jun. 1997.
Wu et al. "Multiparameter Metabolic Analysis Reveals A Close Link Between Attenuated Mitochondrial Beioenergetic Function and Enhanced Glycolysis Dependency in Human Tumor Cells", American Journal of Physiology, Cell Physiology, XP008082046, 292(1): C125-C136, Jan. 1, 2007.
Interview Summary dated Oct. 8, 2021 from US Patent and Trademark Office Re. U.S. Appl. No. 15/724,299. (3 pages).
Notice of Panel Decision from Pre-Appeal Brief dated Aug. 20, 2021 from US Patent and Trademark Office Re. U.S. Appl. No. 15/724,299. (2 pages).
Official Action dated Dec. 27, 2021 from US Patent and Trademark Office Re. U.S. Appl. No. 15/724,299. (17 pages).
Supplementary European Search Report and the European Search Opinion dated Feb. 23, 2021 From the European Patent Office Re. Application No. 18847674.1. (8 Pages).
Advisory Action dated Jun. 11, 2021 from the US Patent and Trademark Office Re. U.S. Appl. No. 15/724,299. (6 pages).
Nielsen et al. "A Novel Assay for Monitoring Internalization of Nanocarrier Coupled Antibodies ", BMC Imunology, 7(24): Oct. 1-15, 2006.
Official Action dated Nov. 20, 2020 From the US Patent and Trademark Office Re. U.S. Appl. No. 15/724,299. (17 Pages).
Ignatius et al. "Presentation of Proteins Encapsulated in Sterically Stabilized Liposomes by Dendritic Cells Initiates CD8+ T-Cell Responses In Vivo", Blood, 96(10): 3505-3513, Nov. 15, 2000.
Final Official Action dated Apr. 7, 2021 from the US Patent and Trademark Office Re. U.S. Appl. No. 15/724,299. (16 pages).
Deutsch et al. "Microplate Cell-Retaining Methodology for High-Content Analysis of Individual Non-Adherent Unanchored Cells in a Population"; Biomed Microdevices, 361-374, Jun. 27, 2006.
Final Official Action dated Jul. 18, 2022 from US Patent and Trademark Office Re. U.S. Appl. No. 15/724,299. (18 pages).
Notice of Reasons for Rejection dated Aug. 2, 2022 From the Japan Patent Office Re. Application No. 2020-511461 and Its Translation Into English. (10 Pages).

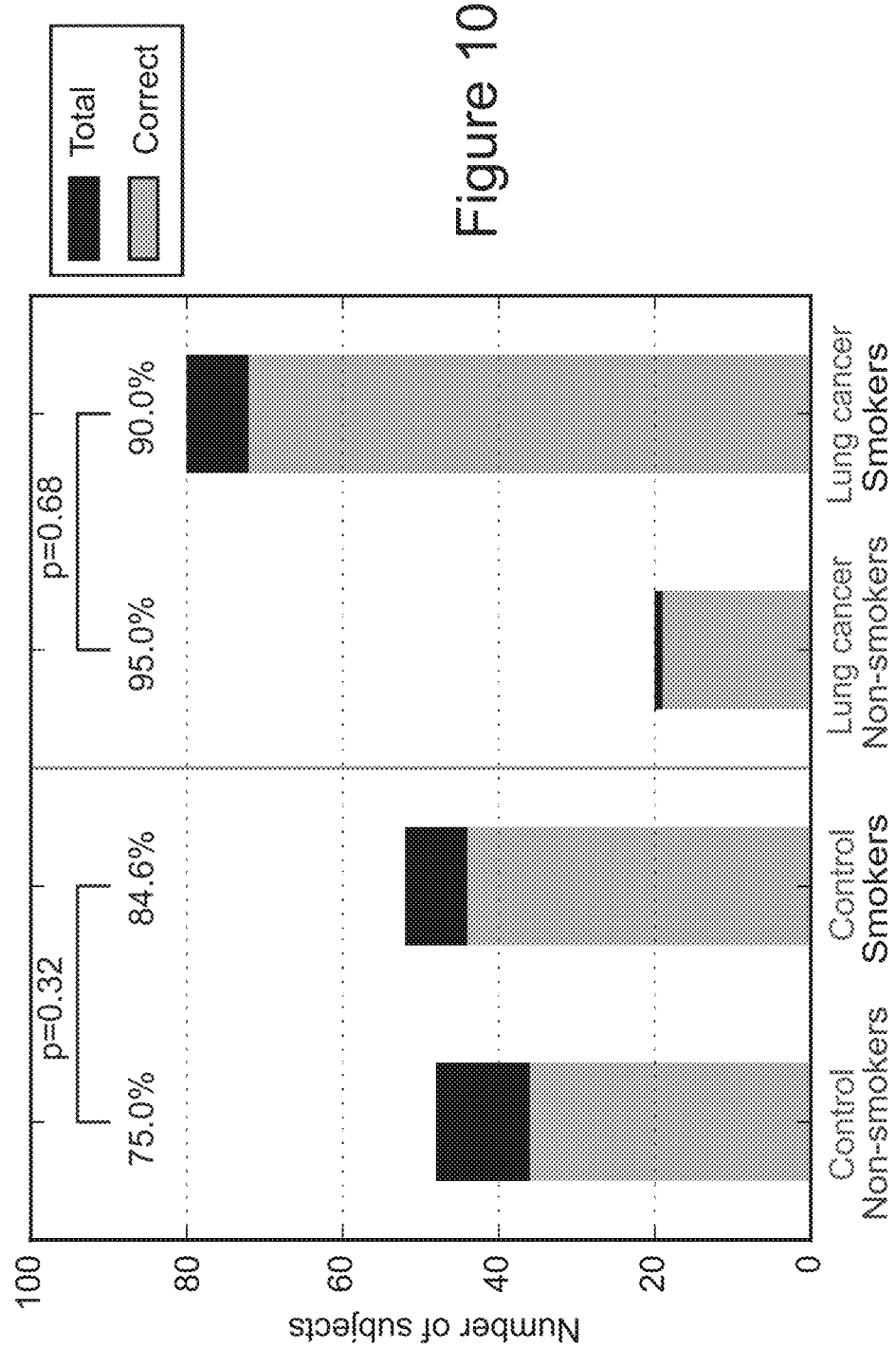

METHODS OF DIAGNOSING AND TREATING LUNG CANCER

RELATED APPLICATIONS

This application is a National Phase of PCT Patent Application No. PCT/IL2018/050920 having International filing date of Aug. 20, 2018, which claims the benefit of priority under 35 USC § 119(e) of U.S. Provisional Patent Application No. 62/547,906 filed on Aug. 21, 2017. The contents of the above applications are all incorporated by reference as if fully set forth herein in their entirety.

SEQUENCE LISTING STATEMENT

The ASCII file, entitled 81164SequenceListing.txt, created on Feb. 20, 2020, comprising 16,371 bytes, submitted concurrently with the filing of this application is incorporated herein by reference. The sequence listing submitted herewith is identical to the sequence listing forming part of the international application.

FIELD AND BACKGROUND OF THE INVENTION

The present invention, in some embodiments thereof, relates to methods of diagnosing and treating lung cancer.

Lung cancer is the third most common cancer diagnosed, but has a higher mortality rate than breast, prostate, and colon cancer combined. Furthermore, since more than half of patients are diagnosed with locally advanced or metastatic disease, and despite advances in treatment, the long-term survival from lung cancer currently remains low. Therefore, significant efforts are being made to make screening and early diagnosis of lung cancer possible, in order to allow early treatment and to improve survival [Smith, R. A. et al. Cancer screening in the United States, 2011. *CA. Cancer J. Clin.* 61, 8-30 (2011); Moyer, V. A. Screening for Lung Cancer: U.S. Preventive Services Task Force Recommendation Statement. *Ann. Intern. Med.* 160, 330-338 (2014)]. The current recommended method for lung cancer screening and early diagnosis by the US Preventive Services Task Force (USPSTF), is chest low dose computed tomography (LDCT) in a high-risk population. This recommendation was based on The National Lung Screening Trial (NLST), which demonstrated that scanning with LDCT led to a 20% reduction in mortality rate in this high-risk population. However, LDCT screening has many limitations, including radiation exposure, high false positive rates and over diagnosis. In addition, the target population of the USPSTF's recommendation represents only about 11% of the 94 million former and current smokers in the U.S. These recommendations also don't take into consideration other high-risk populations, such as patients with chronic obstructive pulmonary disease (COPD), of which about 2.2% develop lung cancer per year. Indeed, there is an urgent need for other non-invasive methods or biomarkers with high accuracy, which might promote an earlier detection of lung cancer, resulting in more efficacious therapeutic interventions and higher likelihood of cure.

Liquid biopsy is a new strategy for the noninvasive detection of cancer using body fluids, mainly blood samples. Several studies include a quantitative analysis to investigate the role of circulating cell-free tumor DNA or non-coding RNA in lung cancer diagnosis. Some methods utilize machine learning to assist the diagnostic process, training a classifier on the covariates obtained from liquid biopsy. Many challenges remain in this approach, including low frequency of secreted tumor components in the blood, their short half-life, cell/DNA fragmentation, high variation in tumor cell mutation, and the incapability to determine tumor origin. Importantly, current methods detect malignancies mostly in advanced stages, in which treatment is less effective.

The Warburg effect is the observation that most cancer cells predominantly produce energy by a high rate of glycolysis followed by lactic acid production in the cytosol, rather than by a comparatively low rate of glycolysis followed by oxidation of pyruvate in mitochondria like most normal cells [Kim J W, Dang C V (2006). "Cancer's molecular sweet tooth and the Warburg effect". *Cancer Res.* 66 (18): 8927-30]. In 1920s Otto Warburg found that cancer cells, in contrast to normal differentiated cells, primarily rely on aerobic glycolysis rather than on mitochondrial oxidative phosphorylation to generate ATP as the fuel for energy needed for cellular processes. This historical phenomenon was termed "the Warburg effect". Otto Warburg postulated that this change in metabolism is the fundamental cause of cancer [Warburg O (1956). "On the origin of cancer cells". *Science* 123 (3191): 309-14], a claim now known as the Warburg hypothesis. About 50 years later the Warburg effect was also observed in activated lymphocytes in vitro see e.g., MacIver et al. 2008 J. Leukocyte Biology 84:1-9; and DeBerardinis Cell Metabolism 7:11-20. The Warburg effect was found also in the immune system where activated T cells rapidly hyperinduce glycolysis, for example by over-expression of glucose transporters (GLUT).

The Warburg effect has important medical applications, as high aerobic glycolysis by malignant tumors is utilized clinically to diagnose and monitor treatment responses of cancers by imaging uptake of $2\text{-}^{18}F\text{-}2\text{-deoxyglucose}$ (FDG) (a radioactive modified hexokinase substrate) with positron emission tomography (PET). See also WO2007/102146. However, these methods are cumbersome and expensive by requiring high-tech facilities or in-situ tissue biopsies.

WO2012/137207 teaches a method of measuring a metabolic activity (MA) of a cell. The method comprises independently measuring in an extracellular environment of the cell, a time-dependent acidification profiles due to secretion of:

(i) non-volatile soluble metabolic products;

(ii) non-volatile soluble metabolic products and volatile soluble metabolic products; or (iii) volatile soluble metabolic products;

wherein at least one of the time dependent acidification profiles is indicative of the metabolic activity of the cell. Also provided are clinical methods which make use of the assay in the diagnosis of cancer.

SUMMARY OF THE INVENTION

According to an aspect of some embodiments of the present invention there is provided a method of diagnosing lung cancer in a subject-in-need thereof, the method comprising:

(a) providing a biological sample of the subject which comprises peripheral blood mononuclear cells (PBMCs);

(b) in vitro contacting the PBMCs with a stimulant selected from the group consisting of the stimulants listed in Tables 3 and 4; and (c) measuring metabolic activity of the PBMCs having been contacted according to (b), wherein a statistically significant change in the metabolic activity of the PBMCs as compared to a control sample is indicative of lung cancer.

According to some embodiments of the invention, the measuring metabolic activity is by measuring extracellular acidification of the PBMCs.

According to some embodiments of the invention, the measuring the extracellular acidification is in an extracellular defined solution having a calibrated buffered capacity of the PBMCs.

According to some embodiments of the invention, the metabolic activity is in a time-dependent manner as a function of a concentration of the stimulant so as to generate an acidification profile.

According to some embodiments of the invention, the acidification profile is due to secretion of:

(i) non-volatile soluble metabolic products and volatile soluble metabolic products;

(ii) non-volatile soluble metabolic products; or (iii) volatile soluble metabolic products.

According to some embodiments of the invention, the measuring the acidification profile of the (ii) is effected in an air-exposed chamber, and wherein measuring acidification profile of the (i) is effected in an air-sealed chamber, and wherein measuring acidification profile of the (iii) is by subtracting an acidification profile of the (ii) from an acidification profile of the (i).

According to some embodiments of the invention, the stimulant is selected from the group consisting of NY-ESO-1, Her-2a, ConA, PHA, MAGE-A3 and glucose.

According to some embodiments of the invention, the measuring is effected in an air-exposed chamber when the stimulant is NY-ESO-1.

According to some embodiments of the invention, the measuring is effected in an air-exposed chamber when the stimulant is Her-2a.

According to some embodiments of the invention, the measuring is effected in an air-exposed chamber when the stimulant is ConA.

According to some embodiments of the invention, the measuring is effected in an air-sealed chamber when the stimulant is PHA.

According to some embodiments of the invention, the measuring is effected in an air-sealed chamber when the stimulant is MAGE-A3.

According to some embodiments of the invention, the measuring is effected in an air-sealed chamber when the stimulant is glucose.

According to some embodiments of the invention, the diagnosing is in which the accuracy of diagnosis has an AUC (area under the curve) of at least 0.6.

According to some embodiments of the invention, the lung cancer is an early stage (1a-2b according to TNM Guideline) lung cancer.

According to some embodiments of the invention, the subject has not been treated with an anti-cancer therapy at least 5 years prior to the measuring.

According to some embodiments of the invention, the measuring is following at least 20 min of contacting with the stimulant.

According to some embodiments of the invention, the measuring the extracellular acidification of the PBMCs is with a non-toxic, membrane-impermeant pH probe.

According to some embodiments of the invention, the probe is Hydroxypyrene-1,3,6-trisulfonic acid (HPTS).

According to some embodiments of the invention, the control sample is of the biological sample with the stimulant and without the probe.

According to some embodiments of the invention, the control sample is of the biological sample without the stimulant.

According to some embodiments of the invention, the measuring the metabolic activity is at 37° C.

According to some embodiments of the invention, the biological sample is devoid of granulocytes.

According to an aspect of some embodiments of the present invention there is provided a method of treating lung cancer, the method comprising:

(a) diagnosing a subject as having lung cancer as described herein;

(b) treating or selecting treatment for the subject with an anti-lung cancer treatment.

According to an aspect of some embodiments of the present invention there is provided a method of monitoring treatment, the method comprising:

(a) treating a subject having lung cancer with an anti-lung cancer treatment;

(b) measuring metabolic activity in PBMCs of the subject by:

(i) in vitro contacting the PBMCs with a stimulant selected from the group consisting of the stimulants listed in Tables 3 and 4; and (ii) measuring metabolic activity of the PBMCs having been contacted according to (b), wherein a shift in the metabolic activity of the PBMCs towards that of a normal healthy cell sample examined under identical conditions is indicative of an efficacious treatment of the disease.

According to an aspect of some embodiments of the present invention there is provided a kit comprising at least one stimulant of Table 3 or 4 and a non-toxic, membrane-impermeant pH probe.

According to some embodiments of the invention, the anti-lung cancer treatment comprises immunotherapy.

According to some embodiments of the invention, the subject exhibits clinical signs of lung cancer.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is an illustration showing an embodiment of the metabolic activity profile (MAP) test process.

FIG. 2 is a graphic presentation of the distribution of lung cancer stages in the studied cohort. Stage 0 refers to adenocarcinoma in-situ [Weissferdt, A. & Moran, C. A. Reclassification of early stage pulmonary adenocarcinoma and its consequences. J. Thorac. Dis. 6, S581-8 (2014); Goldstraw, P. et al. Non-small-cell lung cancer. Lancet 378, 1727-1740 (2011)]; the 'Other' group includes lung cancer types in which stages are not used.

FIG. 3 is a pie graph showing the frequency of various histological types of lung cancer in the studied cohort.

FIG. 4 is a graph showing Calculation or reaction rates. PBMCs were mixed with D-Glucose as a stimulant in several increasing concentrations, and the change in acidity was measured as a function of time. The concentration of $H^+$ in nM units was derived using the formula: $10^{9-pH}$.

FIGS. 5A-B are graphic presentations showing the behavior of average lung cancer (n=100, black) and healthy (n=100, grey) subjects, when observing the reaction rate (r) as a function of stimulant concentration index (C). The specific stimulant is written in the title of each graph, with the plate state in parentheses. Standard error of the mean is shown for each data point. FIG. 5A: examples of differences that were found between the two populations; FIG. 5B: examples where no significant difference was found.

Figure 1:
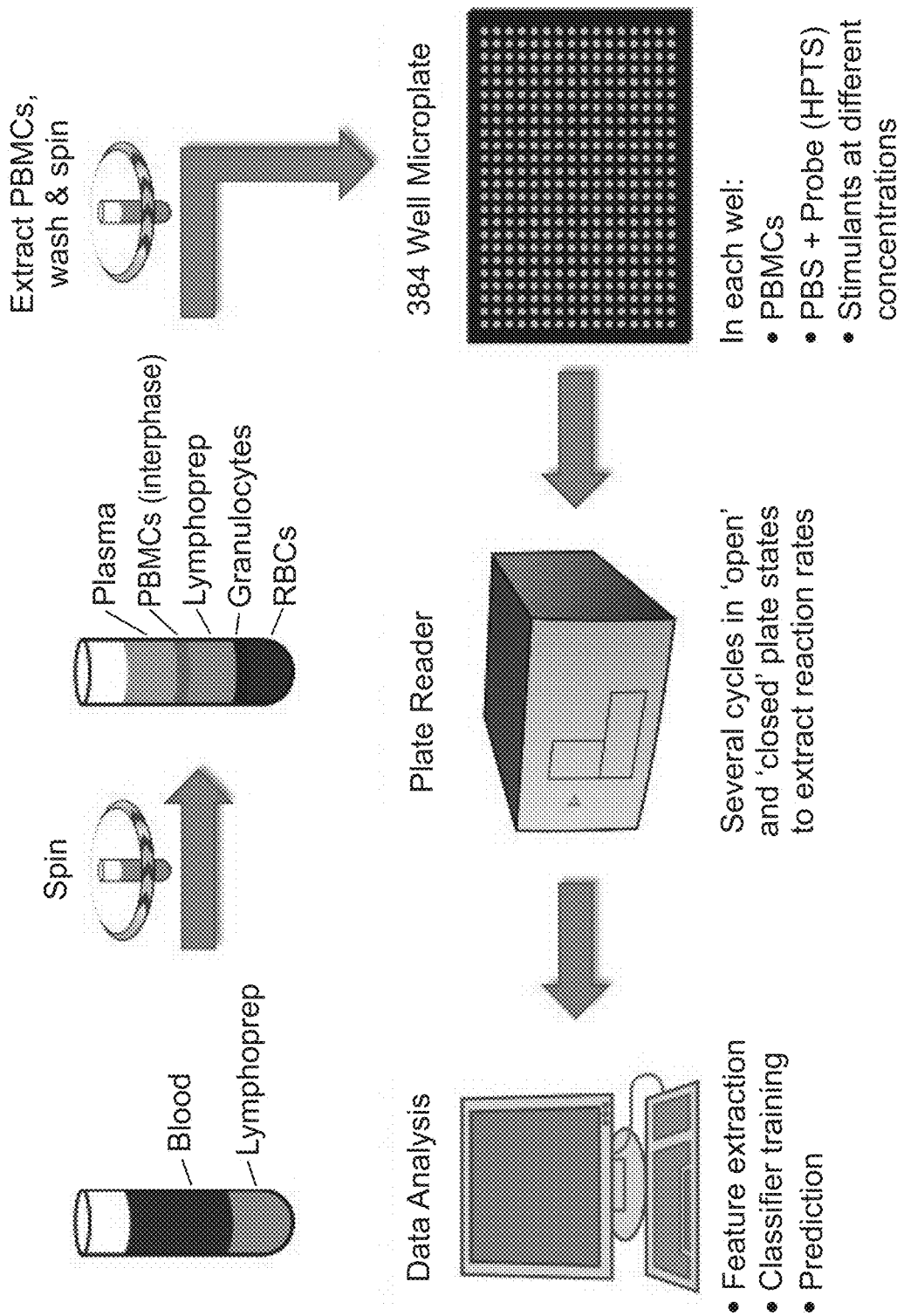

FIG. 10 is a bar graph showing the accuracy of the model, broken down according to subjects' smoking habits. The smokers group also includes former smokers, who have at least one pack-year in their history, but have not smoked in the past 30 days. P-values of the Fisher exact test are shown.

DESCRIPTION OF SPECIFIC EMBODIMENTS OF THE INVENTION

The present invention, in some embodiments thereof, relates to methods of diagnosing and treating lung cancer.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Whilst reducing embodiments of the invention to practice, the present inventors devised a strategy for the diagnosis of lung cancer using a non-invasive blood test. Embodiments of the invention thus relate to the diagnosis of lung cancer by analyzing the metabolic activity of PBMCs in subjects suspected of having cancer. The assay employs in vitro stimulation of PBMCs with lung cancer cell antigens/mitogens and analyzing extracellular acidification profiles as a measure for their metabolic activity. This assay not only allows early detection of cancer, but provides a clinically valuable discrimination between patients with lung cancer versus other diseases that increase immune system activity.

Thus, embodiments of the assay, also referred to as 'Liquid ImmunoBiopsy', refer to a novel functional test that measures the relative acidification levels of the PBMCs extracellular environment, revealing the metabolic activity profiles (MAPs) of the immune system cells as an indicator of disease status. Since the immune system is extremely sensitive, it is inherently suited for early cancer detection.

It is suggested that the resulting detected differences between lung cancer and healthy samples can ultimately be attributed to the differences in PBMC subpopulations and prevalence. In the present assay, the raw MAP test data are firstly analyzed in order to extract meaningful classifier features, which are then used as input parameters for a machine learning diagnostic prediction model. The results provided herewith in the Examples section which follows, present 20-fold cross-validation (CV) results of the diagnostic model, with an AUC of 0.91, displaying high sensitivity and specificity of 91 and 80% respectively. Further and more stringent examinations, using both 10- and 5-fold CV procedures, reveal a slight to no decrease in AUC, which indicates robustness of the presented diagnostic model.

The model demonstrates a statistically uniform sensitivity across different cancer stages, indicating that early detection is possible using the present teachings. This is of a great diagnostic importance, since lung cancer survival is largely and directly dependent on the stage of diagnosis. Moreover, the presence of COPD comorbidity in the tested subjects was shown not to affect the diagnostic results, in either sensitivity or specificity, indicating that the model's results are not influenced by these pathological conditions. COPD increases five-fold the risk for lung carcinogenesis, thus, being able to detect lung cancer in this high-risk population can have a major impact on patient survival.

Results of the assay can be corroborated by the detection of nodules in the lung. It could also potentially be used in high-risk individuals, such as COPD patients. It is suggested that the present approach can be used as a diagnostic tool, in which a negative result will lead to surveillance imaging and the avoidance of unnecessary invasive procedures, while a positive result could lead to an early, life-saving intervention. It is also suggested that embodiments of the assay may contribute to monitoring immuno-responsiveness to immunotherapy procedures, because the MAPs should reflect the expected enhanced immune response.

Thus, according to an aspect of the invention there is provided a method of diagnosing lung cancer in a subject-in-need thereof, the method comprising:

(a) providing a biological sample of the subject which comprises peripheral blood mononuclear cells (PBMCs);

(b) in vitro contacting the PBMCs with a stimulant selected from the group consisting of those listed in Tables 3 and 4 below; and (c) measuring metabolic activity (MA) of the PBMCs having been contacted according to (b), wherein a statistically significant change in the metabolic activity of the PBMCs as compared to a control sample is indicative of lung cancer.

Any of the methods described herein can be used in a diagnostic kit aimed for executing the method.

As used herein "diagnosing" or "diagnosis" refers to determining presence or absence of a pathology (i.e., lung cancer), classifying a pathology or a symptom, determining a severity of the pathology i.e., staging, monitoring pathology progression, forecasting an outcome of a pathology and/or prospects of recovery and screening of a subject for a specific disease.

As used herein, the term "lung cancer" refers to any cancerous growth in the lung. In some embodiments, the lung cancer is small cell lung cancer (SCLC), and non-small cell lung cancer (NSCLC), characterized by the cell size when viewed under the microscope. In other embodiments, primary NSCLC comprises mostly adenocarcinoma (including bronchoalveolar cell carcinoma), squamous cell carcinoma and large cell carcinoma. As used herein, the term lung cancer also includes lung cancers of rare cell types, such as carcinoid tumors and lymphoma. In some embodiments, a lung cancer patient is a patient diagnosed with lung cancer on the basis of imaging, biopsy, staging, etc.

According to a specific embodiment, the lung cancer is NSCLC.

Lung cancer staging is an assessment of the degree of spread of the cancer from its original source. It is one of the factors affecting the prognosis and potential treatment of lung cancer.

The evaluation of non-small-cell lung carcinoma (NSCLC) staging uses the TNM classification. This is based on the size of the primary tumor, lymph node involvement, and distant metastasis.

Using the TNM descriptors, a group is assigned, ranging from occult cancer, through stages 0, IA (one-A), IB, IIA, IIB, IIIA, IIIB and IV (four). This stage group assists with the choice of treatment and estimation of prognosis.

TABLE 2

Stage group according to TNM classification in lung cancer

| TNM | Stage group |
| --- | --- |
| T1a-T1b N0 M0 | IA |
| T2a N0 M0 | IB |
| T1a-T2a N1 M0 | IIA |
| T2b N0 M0 | |
| T2b N1 M0 | IIB |
| T3 N0 M0 | |

TABLE 1

TNM classification in lung cancer

| | T: Primary tumor | | N: Lymph nodes | | M: Metastasis |
| --- | --- | --- | --- | --- | --- |
| TX | Primary tumor cannot be assessed | NX | Regional lymph nodes cannot be assessed | MX | Distant metastasis cannot be assessed |
| Any of: | Tumor cells present in sputum or bronchial washing, but tumor not seen with imaging or bronchoscopy | | | | |
| T0 | No evidence of primary tumor | N0 | No regional lymph node metastasis | M0 | No distant metastasis |
| Tis | Carcinoma in situ | N1 | Metastasis to ipsilateral peribronchial and/or hilar lymph nodes | M1a Any of: | Separate tumor nodule in the other lung Tumor with pleural nodules Malignant pleural or pericardial effusion |
| T1 | Tumor size less than or equal to 3 cm across, surrounded by lung or visceral pleura, without invasion proximal to the lobar bronchus | N2 | Metastasis to ipsilateral mediastinal and/or subcarinal lymph nodes | M1b | Distant metastasis |
| T1a | Tumor size less than or equal to 2 cm across | N3 Any of: | Metastasis to scalene or supraclavicular lymph nodes Metastasis to contralateral hilar or mediastinal lymph nodes | | |
| T1b | Tumor size more than 2 cm but less than or equal to 3 cm across | | | | |
| T2 Any of: | Tumor size more than 3 cm but less than or equal to 7 cm across Involvement of the main bronchus at least 2 cm distal to the carina Invasion of visceral pleura Atelectasis/obstructive pneumonitis extending to the hilum but not involving the whole lung | | | | |
| T2a | Tumor size more than 3 cm but less than or equal to 5 cm across | | | | |
| T2b | Tumor size more than 5 cm but less than or equal to 7 cm across Tumor size more than 7 cm across | | | | |
| T3 Any of: | Invasion into the chest wall, diaphragm, phrenic nerve, mediastinal pleura or parietal pericardium Tumor less than 2 cm distal to the carina, but not involving the carina Atelectasis/obstructive pneumonitis of the whole lung Separate tumor nodule in the same lobe | | | | |
| T4 Any of: | Invasion of the mediastinum, heart, great vessels, trachea, carina, recurrent laryngeal nerve, esophagus, or vertebra Separate tumor nodule in a different lobe of the same lung | | | | |

TABLE 2-continued

Stage group according to TNM classification in lung cancer

| TNM | Stage group |
|---|---|
| T1a-T3 N2 M0 | IIIA |
| T3 N1 M0 | |
| T4 N0-N1 M0 | |
| N3 M0 | IIIB |
| T4 N2 M0 | |
| M1 | IV |

Small-cell lung carcinoma (SCLC) has traditionally been classified as "limited stage" (confined to one-half of the chest and within the scope of a single tolerable radiotherapy field) or "extensive stage" (more widespread disease). However, the TNM classification and grouping are useful in estimating prognosis.

For both NSCLC and SCLC, the two general types of staging evaluations are clinical staging and surgical staging. Clinical staging is performed prior to definitive surgery. It is based on the results of imaging studies (such as CT scans and PET scans) and biopsy results. Surgical staging is evaluated either during or after the operation and is based on the combined results of surgical and clinical findings, including surgical sampling of thoracic lymph nodes.

Any of these methods can be used to corroborate the diagnosis according to the present teachings or as to provide a first diagnosis.

According to a specific embodiment, the lung cancer is an early stage lung cancer (e.g., TNM 1a-2b).

As used herein, the term "subject" refers to a subject (e.g., human) being tested by the methods or kits of the present invention. The subject can be a subject who is at risk of having lung cancer [e.g., a genetically predisposed subject, a subject of advanced age, a subject with medical and/or family history of cancer, a subject suffering from COPD, a subject who has been exposed to smoke and/or other carcinogens, occupational hazards, environmental hazards] and/or a subject who exhibits suspicious clinical signs of lung cancer or cancer in general [e.g., persistent cough, hemoptysis, chest pain, shortness of breath, pleural effusion, wheezing, hoarseness, recurrent bronchitis or pneumonia, bone pain, paraneoplastic syndromes, unexplained pain, sweating, unexplained fever, unexplained loss of weight up to anorexia, anemia and/or general weakness]. Additionally or alternatively, the subject can be a healthy human subject undergoing a routine well-being check-up or routine screen of a random or representative population. The subject can also be a patient or subject participating in an investigation or test. The subject can be a smoker or non-smoker or former smoker (as shown in Example 5).

According to some embodiments of the invention, the lung cancer is an early stage (1a-2b according to TNM Guideline) lung cancer.

According to some embodiments of the invention, the subject has not been treated with an anti-cancer therapy at least 2-5 years prior to the measuring.

According to some embodiments of the invention, the subject has not been treated with an anti-cancer therapy at least 2 years prior to the measuring.

According to some embodiments of the invention, the subject has not been treated with an anti-cancer therapy at least 3 years prior to the measuring.

According to some embodiments of the invention, the subject has not been treated with an anti-cancer therapy at least 4 years prior to the measuring.

According to some embodiments of the invention, the subject has not been treated with an anti-cancer therapy at least 5 years prior to the measuring.

In accordance with other embodiments/aspects of the invention, the subject is already diagnosed with lung cancer or has such a suggested diagnosis (e.g., effected by chest radiography, CT imaging, bronchoscopy, CT-guided biopsy and/or histopathology) and the present assay is used to corroborate the diagnosis, optimize treatment or monitor treatment.

According to a specific embodiment, the subject is not diagnosed with cancer (e.g., any cancer).

According to an alternative or an additional embodiment, the subject has not been treated with an anti-cancer therapy (dedicated therapy) at least 0.5-5 years prior to the measuring of the metabolic activity.

As used herein "metabolic activity pathway" refers to the relative contribution of mitochondrial oxidative phosphorylation, anaerobic glycolysis, aerobic glycolysis and $NH_3^+$ production to energy production.

The profiles may have a spike configuration or a monotonic saturated behavior.

A spikes profile typically reflects receptor mediated stimulation of metabolic activity which is expected to be more specific compared to the concentration dependent nutrient response. The latter response is generally a monotonic saturated profile.

As used herein "cell" refers to a white blood cell, e.g., peripheral blood mononuclear cell (PBMC), selected from the group consisting of lymphocytes, (e.g., T cells, B cells, NK cells) and monocytes. Thus, the sample can comprise whole blood or depleted of some blood components such as granulocytes, platelets and/or erythrocytes, i.e., fractionated blood. According to a specific embodiment, the sample comprises $1000-10^7$ cells (e.g., $10^4-10^7$ cells/ml e.g., $5*10^6$ cells/ml e.g., $5*10^4$ cells/ml.

According to a specific embodiment the cells comprise PBMCs.

According to a specific embodiment the cells comprise a pure population of PBMCs e.g., >80% (e.g., by Ficoll).

Methods of depleting blood components e.g., red blood cells, are known in the art and include for example hemolysis, centrifugation, sedimentation, filtration or combinations thereof.

FIG. 1 and the Example section below describes a specific embodiment of such a fractionation process.

Thus, the cell may refer to an isolated population of cells which comprise a highly purified subset of specific cells i.e., homogenic cell population (e.g., >80% purity), e.g., T cells, or a heterogenic cell population which comprises various types of immune cells such as peripheral blood leukocytes (PBL) or peripheral blood mononuclear cells (PBMCs).

According to a specific embodiment, the cell is in a pure population of cells i.e., pure population of PBMCs i.e., more than 70% PBMCs, more than 80% PBMCs, more than 90% PBMCs, more than 95 PBMCs.

As the measurement of metabolic activity is effected in real time, it is important that the cells are maintained viable.

According to a specific embodiment, the cells are assayed immediately after retrieval from the subject, i.e., not more than 2-4 hours (e.g., 3 hours) following blood retrieval.

According to other embodiments, the cells are stored prior to examination (e.g., at 4° C. or cryo-preserved). According to some embodiments, the cells are stored at 18° C. When the cells are introduced to stimulants, on plate, the plate is loaded on ice e.g 4° C., followed by reading at it in 37° C.

According to a specific embodiment, the cell is not a cell line.

As mentioned, once the cells are at hand they are in vitro contacted with a stimulant.

As used herein "stimulant" refers to an entity that increases, decreases or changes a metabolic pathway of a cell in response thereto.

For instance, if the cell is a lymphocyte then the stimulant is an antigen that is recognized by the TCR or BCR and leads to clonal expansion or antibody production. Specific stimulants or inhibitors are listed in Tables 3 and 4 below.

It will be appreciated that one of more stimulant (e.g., 2, 3, 4) at the same or different concentrations can be used for a single sample or for a single aliquot of a sample for determining the metabolic activity and optionally determining the profiles as described herein. For example, different Her2 peptides or different stimulants all together e.g., PMA and Her2 peptides can be used.

TABLE 3 list of stimulants including general stimulants of the immune system, specific stimulants to cancer and lung cancer and nutrients such as glucose and L-glutamine. The suffix 'aa' signifies a range of amino acid positions. Items marked with * are proteins in which only a partial sequence e.g., of ~20 amino acids can be used.

| Stimulant | Exemplary Concentration range |
| --- | --- |
| Phytohaemagglutinin (PHA) e.g., Sigma L4144 | 0-100 µg/ml |
| Concanavalin A (CON A) e.g., - Sigma C0412 | 0-100 µg/ml |
| Phorbol Myristate Acetate (PMA) e.g., Sigma P1585 | 0-10 ng/ml |
| Lipopolysaccharide (LPS) e.g., Sigma L6529 | 0-10 ng/ml |
| Rapamycin e.g., - Sigma R8781 | 0-50 mM |
| D-Glucose e.g., Sigma G8769 | 0-10 mM |
| L-glutamine e.g., biological industries 03-020-1C | 0-10 mM |
| Myelin-Basic-Protein (MBP) * Exemplary sequences: 1: HGRTQDENPVVHFFKNIVTPRTPPPS/SEQ ID NO: 1 2: ENPVVHFFKNIVTPRTPPPSQ/SEQ ID NO: 2 3: TENPVVHFFKNIVTPRTPPPSQGKGRG/SEQ ID NO: 3 4: VHFFKNIVTPRTP/SEQ ID NO: 4 5: DENPVVHFFKNIVTPRTPPPSQGKGR/SEQ ID NO: 5 | 0-100 µg/ml |
| Carcinoembryonic antigen (CEA)* e.g., Ea, Eb Exemplary sequences: Carcinoembryonic antigen CEA (Ea) 1: PPDSSYLSGANLNLSCHSASN/SEQ ID NO: 6 2: YLSGANLNL/SEQ ID NO: 7 3: IISPPDSSYLSGANLNLSCH/SEQ ID NO: 8 4: TPIISPPDSSYLSGANLNLSCHSASNPSP/SEQ ID NO: 9 5: PPDSSYSLGANLNLSCHSASN/SEQ ID NO: 10 6: YSLGANLNL/SEQ ID NO: 11 7: IISPPDSSYSLGANLNLSCH/SEQ ID NO: 12 8: TPIISPPDSSYSLGANLNLSCHSASNPSP/SEQ ID NO: 13 Carcinoembryonic antigen CEA (Eb) 1: IAKITPNNNGTYACFVSNLATGRNNSIVK/SEQ ID NO: 14 2: PNNNGTYACFVSNLATGRNNS/SEQ ID NO: 15 3: ITPNNNGTYACFVSNLATGR/SEQ ID NO: 16 4: TYACFVSNL/SEQ ID NO: 17 | 0-100 µg/ml |
| Mucin 1 (MUC-1)* Exemplary sequences MUC-1 Ub: 1: PDTRPAPGSTAPPAHGVTSA/SEQ ID NO: 18 2: APPAHGVTSAPDTRPAPGSTAPPAHGVTSAPDTRPAPGST/SEQ ID NO: 19 3: GVTSAPDTRPAPGSTAPPAHGVTSAPDTRP/SEQ ID NO: 20 4: AHGVTSAPDTRPAPGSTAPPAHGVTSAPDTRPAPG/SEQ ID NO: 21 | 0-100 µg/ml |
| New York esophageal squamous cell carcinoma 1 (NY-ESO-1)* Exemplary sequences: 1: RCGARGPESRLLEFYLAMPFATPMEAELARRSLAQDAPPL/SEQ ID NO: 22 2: SRLLEFYLAMPFATPMEAELARRSLA/SEQ ID NO: 23 3: GPESRLLEFYLAMPFATPMEAELARRSLAQDA/SEQ ID NO: 24 4: LLEFYLAMPFATPMEAELAR/SEQ ID NO: 25 | 0-100 µg/ml |
| Melanoma-associated antigen A3 (MAGE-A3)* Exemplary sequences (ML): 1: GSDPACYEFLWGPRALVET/SEQ ID NO: 26 2: FLWGPRALV/SEQ ID NO: 27 3: EFLWGPRALVETSYVKV/SEQ ID NO: 28 4: VPGSDPACYEFLWGPRALVETSYVKVLHH/SEQ ID NO: 29 | 0-100 µg/ml |
| Cytokeratin 19 CYFRA 21-1* e.g., BA1016S (AcrisAntibody) | 0-1 µg/ml |
| Gastrin-releasing peptide (GRP) Exemplary sequences (GRa): 1: RAVPLPAGGGTVLTKMYPRGNHWAVGHLMGKKS/SEQ ID NO: 30 2: LAPRGRAVPLPAGGGTVLTKMYPRGNHWAVGHLMGK/SEQ ID NO: 31 3: VPLPAGGGTVLTKMYPRGNHWAVGHLM/SEQ ID NO: 32 4: VLCLAPRGRAVPLPAGGGTVLTKMYPRGNHWAVGHLMGKKSTGESSS/SEQ ID NO: 33 | 0-100 µg/ml |

TABLE 3-continued list of stimulants including general stimulants of the immune system, specific stimulants to cancer and lung cancer and nutrients such as glucose and L-glutamine. The suffix 'aa' signifies a range of amino acid positions. Items marked with * are proteins in which only a partial sequence e.g., of ~20 amino acids can be used.

| Stimulant | Exemplary Concentration range |
|---|---|
| Exemplary sequences (GRb): | |
| 1: MYPRGNHWAVGHLM/SEQ ID NO: 34 | |
| 2: PAGGGTVLTKMYPRGNHWAVGHLMGKK/SEQ ID NO: 35 | |
| 3: RGRAVPLPAGGGTVLTKMYPRGNHWAVGHLMGKKSTGES/SEQ ID NO: 36 | |
| 4: GGTVLTKMYPRGNHWAVGHLMGKKSTGES/SEQ ID NO: 37 | |
| Her2/neu* | 0-100 μg/ml |
| Exemplary sequences (Ha): | |
| 1: Palmitoyl -KTTKS/SEQ ID NO: 38 | |
| Exemplary sequeneces (Hb): | |
| 1: KFPDEEGACQPCPINCTHSCVDLD/SEQ ID NO: 39 | |
| 2: GACQPCPINCTHSCVDLDDKGC/SEQ ID NO: 40 | |
| 3: IWKFPDEEGACQPCPINCTHSCVDLDDKGC/SEQ ID NO: 41 | |
| 4: CQPCPINCTH/SEQ ID NO: 42 | |

TABLE 4

| Stimulants | |
|---|---|
| Pro-surfactant protein B (Pro-SFTPB) | |
| Diacetylspermine (DAS) | |
| G antigen (GAGE, CTA4) | Exemplary sequences:<br>1: MSWRGRSTYYWPRPRRYVQPPEMIGPM/SEQ ID NO: 43<br>2: STYYWPRPRRYVQPP/SEQ ID NO: 44<br>3: GRSTYYWPRPRRYVQPPEMI/SEQ ID NO: 45<br>4: YYWPRPRRY/SEQ ID NO: 46<br>5: YRPRPRRY/SEQ ID NO: 47 |
| HuD | Exemplary Sequences:<br>1: LVRDKITGQSLGYGFVNYIDPKDAEKAIN/SEQ ID NO: 48<br>2: GQSLGYGFVNYIDPKD/SEQ ID NO: 49<br>3: LGYGFVNYI/SEQ ID NO: 50<br>4: DKITGQSLGYGFVNYIDPKDAEK/SEQ ID NO: 51 |
| A Kinase Anchor Protein 4 (AKAP4, CTA99) | |
| Pituitary Tumor-Transforming 1 (PTTG1, Securin) | |
| Annexin I | |
| 14-3-3ζ & 14-3-3σ | |

MHC-restricted peptide antigens from the above mentioned polypeptides are provided herein below.

The stimulant may be diluted at various concentrations or a single concentration may be used.

Measuring of the metabolic activity can be effected throughout the contact with the stimulant.

For example, measuring can be done as soon as the stimulant is added and for at least 120-180 min. For example, measuring can be effected for 1-2 hours (e.g., 1.5 h) following addition of the stimulant to the cells.

According to a specific embodiment, measuring metabolic activity of the cells is by measuring extracellular acidification of the cells (e.g., PBMCs).

Accordingly, the measuring the extracellular acidification is in an extracellular defined solution having a calibrated buffered capacity of the PBMCs.

According to a specific embodiment, the measuring the metabolic activity is in a time-dependent manner as a function of a concentration of the stimulant so as to generate an acidification profile, which represents the relative acidification rate.

According to a specific embodiment, the acidification profile is due to secretion of:

(i) non-volatile soluble metabolic products and volatile soluble metabolic products;

(ii) non-volatile soluble metabolic products; or (iii) volatile soluble metabolic products.

According to a specific embodiment, the measuring the acidification profile of the (ii) is effected in an air-exposed chamber, and wherein measuring acidification profile of the (i) is effected in an air-sealed chamber, and wherein measuring acidification profile of the (iii) is by subtracting an acidification profile of the (ii) from an acidification profile of the (i).

Thus, according to certain embodiments, in order to achieve a sensitive measure, a non-toxic, membrane-impermeant pH indicator/probe is used that can sense minor pH changes at about physiologic pH (~7.4).

Examples include, but are not limited to, a ratiometric pH probe, a $CO_2$ probe, an $NH_3$ probe, a lactate probe and a combination of same. According to a specific embodiment the ratiometric technique is required for the high sensitivity at pH buffered conditions.

Examples of specific probes which can be used according to the present teachings include, but are not limited to, 8-Hydroxypyrene-1,3,6-trisulfonic acid (HPTS), CFDA and carboxy fluorescein. Such probes are commercially available such as from Molecular Probes.

According to a specific embodiment, measuring the acidification is effected using the ratiometric pH probe 8-Hydroxypyrene-1,3,6-trisulfonic acid (HPTS).

HPTS has a pKa of ~7.3 in aqueous buffers is used. HPTS exhibits a pH-dependent absorption shift, allowing ratiometric pH measurements as function of the ratio between the fluorescence intensities at 513 nm that are measured sequentially under excitation at 455 nm and 403 nm.

Extracellular monitoring may be facilitated by attachment of ratiometric molecular optical probes to nanoparticles to avoid intracellular effects.

Any of the above acidification profiles can be used as an indicator of the metabolic activity of the cell. Alternatively, only one of the measured profiles is indicative of the metabolic activity of the cell.

A calibration curve is typically generated with known pH values (containing the same amount of probe).

The calibration curve is constructed for the same measures e.g., 'open' and/or 'closed' states (as described herein), allowing pH measurement as a function of the ratio between the two excitation wavelengths.

According a specific embodiment, one measure i.e., in a sealed (closed) or open chamber is sufficient to determine the metabolic activity relative to a control sample (under the same conditions).

According a specific embodiment, two measures i.e., in a sealed (closed) and open chambers are sufficient to determine the metabolic activity relative to a control sample (under the same conditions).

According a specific embodiment, all measures i.e., in a sealed (closed) and open chambers as well as the subtraction are necessary to determine the metabolic activity relative to a control sample (under the same conditions).

As used herein "independently measuring" refers to separate measuring of items (i), (ii) and possibly (iii). Although it will be appreciated, according to a specific embodiment, that (iii) is the result of subtracting (ii) from (i). These separate measurements can be performed in parallel, simultaneously, on identical yet separate cell samples, or sequentially on a single cell sample (as described in the Examples section which follows).

Thus, measuring extracellular acidification profile is performed by the calibrated curve of acidification.

Measurement of metabolic activity is performed by calculating the accumulated acidification in relation to the fluorescencently measured pH changes in the extracellular environment of the cells (e.g., nM/min of H+ concentration) in "open" and "close" state. It will be appreciated that, according to a specific embodiment, this measurement is performed only in the extracellular environment of the cell and not intracellularly. Extracellular pH measurement is advantageous since in the extracellular environment there is a persistent acidic accumulation versus a relatively small average changes in the transient intracellular responses due to homeostatic physiological regulation; there is no physiological interference of the extracellular probe with intracellular processes; there is a comparative high signal to noise ratio of the extracellular ratiometric fluorescent probe; simplicity of fluorescent medium (calibrated buffer capacity) preparation versus cellular manipulations; there is no background fluorescence in contrast to significant leakage of intracellular probes; kinetic measurements are made with no need for permeabilization procedures, thereby allowing the analysis of live cells in real-time; there are minimal problems associated with quenching and oxidation effects; and finally simultaneous high throughput kinetic measurements are enabled without the above hurdles.

According to a specific embodiment, the MA test is effected in a defined solution (all components are known) having a calibrated buffered capacity.

It will be appreciated that the buffer capacity should ensure minor changes in the physiological pH.

According to a specific embodiment, the buffer is a phosphate buffer (e.g., phosphate buffer saline 1-10 mM or 10 mM phosphate buffer). It will be appreciated that low buffer concentration is required for acidification measurements at low cell concentration. According to a specific embodiment 10 mM phosphate buffer saline is used for $5 \times 10^6$ cells/ml (e.g., purified PBMCs).

According to a specific embodiment, measuring the acidification profiles is performed at a constant temperature, e.g., 20-40° C. or specifically, at optimal growth temperature, say 37° C. for PBMCs.

As mentioned, all measures are made with respect to control sample(s). For instance, as for the test assay just without the stimulant (representing basal state); alternatively or additionally without the cells; and/or without the cells and the stimulant).

It will be appreciated that each assay can employ one stimulant or more in the same chamber/well or in separate chambers/wells.

Thus, a single blood sample can be subjected to a panel of stimulants (e.g., 2-25, 2-20, 2-10, 2-5, 2-4).

According to a specific embodiment, the stimulant is selected from the group consisting of NY-ESO-1, Her-2a, ConA, PHA, MAGE-A3 and glucose.

According to a specific embodiment, the measuring is effected in an air-exposed chamber when the stimulant is NY-ESO-1.

According to a specific embodiment, the measuring is effected in an air-exposed chamber when the stimulant is Her-2a.

According to a specific embodiment, the measuring is effected in an air-exposed chamber when the stimulant is ConA.

According to a specific embodiment, the measuring is effected in an air-sealed chamber when the stimulant is PHA.

According to a specific embodiment, the measuring is effected in an air-sealed chamber when the stimulant is MAGE-A3.

According to a specific embodiment, the measuring is effected in an air-sealed chamber when the stimulant is glucose.

As described hereinabove, the extracellular acidification profiles are indicative of the identity of the various metabolic products secreted by the cell.

A lung tumor uses preferentially aerobic glycolysis which is characterized mainly by the secretion of Lactate (non-volatile) to the medium. In contrast, a differentiated tissue employs oxidative phosphorylation or anaerobic glycolysis and therefore secretes $CO_2$ (volatile) or lactate, dependent on the availability of oxygen, respectively.

According to a specific embodiment, a time dependent acidification profile due to secretion of non-volatile soluble metabolic products mainly lactate is performed in an air-exposed chamber. Under such conditions ("open"), there is gas ventilation of $CO_2$ and $NH_3$, so that only lactate acid production (including other non-volatile organic acids) contributes to the equivalent acidic accumulation in each well.

According to a specific embodiment, time dependent acidification profile due to secretion of non-volatile soluble metabolic products and volatile soluble metabolic products is effected in an air-scaled chamber. In the hermetically scaled state ("close"), $CO_2$ and $NH_3$ react at equilibrium with water to form carbonic acid and basic ammonium ions. In this state, however, the $NH_4^+$ basic cation titrates the acidity level produced by both the lactic and carbonic acid anions around pH 7.

According to a specific embodiment, the acidification kinetics is measured in 20-100 minutes e.g., 50 minutes per mode sequence of air "open" and "closed" states of the multi well plate.

By the appropriate rates (V), of acidification (+) and basic titration (−), the total measured rates of acidification in the open state (Vopen) and the closed state (Vclosed) are described by the coupled equations:

Vopen=V(lactic acid).

Vclose=V(lactic acid)+V(carbonic acid)−V(ammonium base).

Using this configuration, the time-dependent acidification profile due to secretion of volatile soluble metabolic products can be calculated by the subtraction of the profiles of (ii)-(i).

High throughput screening can be performed using a multi well plate, a multi well plate reader (for detecting the fluorescent signal, e.g., available from TECAN), a CCD camera applying image analysis or fiber optics matrices.

Once acidification profiles are obtained (e.g., with or without stimulant/inhibitor), the profile(s) are recorded. A statistically significant shift (i.e., a change) in the metabolic activity between the cells of the subject and those of the control (e.g., as described above), under identical conditions, is indicative of lung cancer.

Raw data is subject to machine learning which may employ classifiers, such as decision tree models, logistic models and or support vector machines (SVM), which classify the results and assist in the design of the product used in diagnosis. According to some embodiments, bagging can be employed by training an ensemble of such classifiers on random subsets of the cohort, followed by aggregating their individual predictions using hard voting. A specific embodiment is described in the Examples section under "Data Analysis".

According to an embodiment of the invention, the resultant acidification profiles are recorded and stored in a database such as on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

Embodiments of the diagnostic method/kit described herein provide an acceptable level of clinical or diagnostic accuracy. Using such statistics, an "acceptable degree of diagnostic accuracy", is herein defined as a test or assay (such as the test used in some aspects of the invention for determining the clinically significant change/shift in metabolic activity, which thereby indicates lung cancer) in which the AUC (area under the ROC curve for the test or assay) is at least 0.6, desirably at least 0.65, more desirably at least 0.8, preferably at least 0.85, more preferably at least 0.9, and most preferably at least 0.95.

By a "very high degree of diagnostic accuracy", it is meant a test or assay in which the AUC (area under the ROC curve for the test or assay) is at least 0.75, 0.80, desirably at least 0.85, more desirably at least 0.875, preferably at least 0.90, more preferably at least 0.925, and most preferably at least 0.95.

Alternatively, the methods predict the presence of a lung cancer or response to therapy with at least 75% sensitivity, more preferably 80%, 85%, 90%, 95%, 97%, 98%, 99% or greater sensitivity.

Alternatively, the methods predict the presence of lung cancer or response to therapy with at least 75% specificity, more preferably 80%, 85%, 90%, 95%, 97%, 98%, 99% or greater specificity.

The robustness and accurateness of the present methodology suggests its use in numerous clinical applications.

Thus, there is provided a method of treating lung cancer, the method comprising:

(a) diagnosing a subject as having lung cancer as described herein (b) treating or selecting treatment for said subject with an anti-lung cancer treatment.

The method may further comprise corroborating the diagnostic results as described herein using Gold standard methods, when needed.

Treatment of lung cancer typically depends on the stage and type of the disease. The skilled artisan will readily know the treatment options that may be available. Following is a non-restrictive list:

Surgery with removal of the entire lobe in which the tumor is located, is the primary treatment for patients with early-stage cancer who are in good general health. The goal of surgery is to totally eliminate all the tumor cells and thereby provide a cure.

Radiation therapy, or radiotherapy, delivers high-energy x-rays that can destroy rapidly dividing cancer cells. It has many uses in lung cancer:

As primary treatment;

Before surgery to shrink the tumor;

After surgery to eliminate any cancer cells that remain in the treated area;

To treat lung cancer that has spread to the brain or other areas of the body;

Lobectomy—removal of an entire lobe of the lung—is an accepted procedure for removing lung cancer when the lungs are functioning well.

In brachytherapy, radiation is delivered directly to the site of disease. This is usually achieved either through a surgical procedure where after resection of the primary tumor radioactive seeds are sutured to the edge of the surgical resection.

Chemotherapy involves drugs that are toxic to cancer cells. The drugs are usually given by direct injection into a vein or through a catheter placed in a large vein. Often given after surgery to sterilize microscopic disease, chemotherapy also may slow tumor growth and relieve symptoms in patients who cannot have surgery. Newer biologic agents, which may have fewer side effects than traditional chemotherapy and in some instances may be just as effective, are being used. This treatment is used in all stages of lung cancer and can prolong life even in elderly persons as long as they are in good general health. Some chemotherapy drugs increase damage done to tumors by the radiation treatment of cancer cells. Others keep the tumor cells at a stage where they are most susceptible to radiation treatment, or impair the ability of cancer cells to repair themselves after a course of radiation therapy.

Radiation therapy is the delivery of focused high-energy x-rays (photons), gamma rays or atomic particles. It affects cells that are rapidly dividing—such as cancer cells—much more than those that are not.

Immunotherapy uses drugs that boost the patient's immune system to help control cancer. Some studies, but not all, have shown better survival rates when these drugs are given after surgery. Examples of immunotherapy include, but are not limited to, monoclonal antibodies, immune checkpoints inhibitors, cancer vaccines and non-specific immunotherapy.

Gene therapy may kill cancer cells or slow their growth when healthy genes are delivered directly into a lung tumor.

Angiogenesis inhibitors are agents that prevent new blood vessels from forming in growing cancers and may actually turn off the tumor's blood supply. This remains an experimental approach but is promising in part because it seems to cause very few side effects.

Genetic testing is being evaluated in order to select patients for appropriate treatment (e.g., mutations in EGFR).

Stereotactic Body Radiation Therapy (SBRT) can control early-stage tumors at a rate that is comparable to that achieved by surgery.

According to a specific embodiment, the treatment is by immunotherapy, which may be specifically suited for the method of monitoring described herein as these drugs work on the immune system which the present teachings analyze.

Accordingly, there is provided a method of monitoring treatment, the method comprising:

(a) treating a subject having lung cancer with an anti-lung cancer treatment;

(b) measuring metabolic activity in PBMCs of the subject by:

(i) in vitro contacting said PBMCs with a stimulant selected from the group consisting of the stimulants listed in Tables 3 and 4; and (ii) measuring metabolic activity of said PBMCs having been contacted according to (b), wherein a shift in the metabolic activity of the PBMCs towards that of a normal healthy cell sample examined under identical conditions is indicative of an efficacious treatment of the disease. For example, it is suggested that in the metastatic phase the MA profile might regress close to the normal profile.

Any of the methods of treating/monitoring treatment or determining treatment (personalized therapy) can be effected as used herein for the diagnosis in terms of determining the metabolic activity of the PBMCs.

The present teachings further refer to a kit which comprises the stimulants as described herein (e.g., at least 1, at least 2, at least 3 at least 4, at least 5, at least 6, at least 7, at least 8, of the stimulants listed in Table 3 or 4). The kit may further comprise a probe as described herein, a plate (suitable for reading in a fluorescent detector), a buffer for the PBMCs and/or instructions for use.

The pack kit may be packed, for example, by a metal or plastic foil, such as a blister pack. The pack may be accommodated by a notice associated with the container in a form prescribed by a governmental agency regulating the manufacture, use or sale of pharmaceuticals, which notice is reflective of approval by the agency of the form of the compositions or human or veterinary use. Such notice, for example, may be of labeling approved by the U.S. Food and Drug Administration for diagnostic kits.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perhal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Study Design, Demographics and Protocol

Subjects were enrolled between June 2014 and December 2016 in three medical centers: Carmel Medical Center (Haifa), Rambam Medical Center (Haifa) and Sourasky Medical Center (Tel Aviv). In all cases, the study received Helsinki approval from the institutional Review Board (approval numbers: 0105-13-CMC, 0274-15-RMB and 0009-13-TLV respectively). Subjects read and signed a dedicated consent form. Inclusion criteria included 18≤age≤90 years, no pregnancy and no treatment for lung cancer prior to blood withdrawal. Exclusion criteria included treatment for any type of malignancy in prior 5 years, clinically determined active infection or inflammation, treatment with medication that can affect the immune system, lactation or ongoing fertility treatment, or any of the following conditions: HIV positive, hepatitis B/C, autoimmune disease, hypersensitivity and/or allergy that cannot be avoided. Lung cancer and healthy (non-lung-cancer) subjects were enrolled in parallel, the reference standard for lung cancer being biopsy or surgery. Once the number of lung cancer subjects reached 100, they were matched with healthy subjects via an automated process to obtain a balanced 1:1 cohort, with an optimal matching of age, gender and COPD distributions, resulting in a total sample size of 200, as described in Table.

Collection and Separation of PBMCs

Blood samples were collected in 9 ml Vacutubes with EDTA (Greiner Bio-One 455036). For a high viability rate of the blood cells, the samples were transported in thermostated containers set to 18° C. until PBMCs separation. PBMCs were isolated by Lymphoprep™ kit, according to manufacturer's instructions (Axis-Shield).

MAP Test Preparation and Measurement

Each well in a black non-binding, low-volume 384 multi-well plate (Greiner Bio-One) was loaded with 10 µl of the PBMCs solution and 10 µl of 10 mM phosphate buffered saline (PBS) containing 8-Hydroxypyrene-1,3,6-trisulfonic acid (HPTS, Sigma-Aldrich Ltd.), and including one of 14 stimulating reagents (stimulants) in increasing concentrations. The final concentration of the HPTS probe in each well was 0.5 µM, and the final concentration of the PBMCs was $5 \cdot 10^6$ cells/ml in 10 mM PBS. Buffer capacity was specifically matched to allow for pH changes to occur as a result of PBMC metabolic activity. Each well was seeded with $5 \cdot 10^6$ cells/ml, in order to reflect the average PBMC concentration in adult peripheral blood. The samples were loaded in triplicates, first PBMC samples, followed by stimulants, to obtain a final volume of 20 µl in each well. Furthermore, each test included two controls: one containing only the fluorescent HPTS probe, without cells and without stimulants; the other containing the HPTS probe with cells but without stimulants, which represents the 'basal state'. The acidification process was monitored for approximately 1.5 hours at 37° C. by a commercial fluorescence scanner (TECAN Infinite M200). First, the scanner monitored the acidification process without a plate seal ('open' state), and then the multi-well plate was sealed hermetically (ThermalSeal RT™, Excel Scientific, Inc.) to avoid ventilation of $CO_2$ and $NH_3$ for the second phase of the test ('closed' state). Analysis of the profiles was done sequentially. Both states enable the measurement of real-time accumulation of 'soluble' versus 'volatile' metabolic products. The fluorescence intensities were measured at 513 nm under sequential excitation at wavelengths of 455 nm and 403 nm. See a graphical illustration of the process in FIG. 1. The PBMCs do not include granulocytes.

Measurement of pH Using HPTS Fluorescent Probe

The fluorescent probe HPTS is a non-toxic, membrane-impermeant pH indicator, with a pKa of ~7.3 in aqueous buffers. HPTS exhibits a pH-dependent absorption shift, allowing ratio-metric pH measurements as a function of the ratio between the fluorescence intensities measured at a wavelength of 513 nm, under excitation at wavelengths of 455 nm and 403 nm sequentially. The calibration curve used in the MAP test comprised PBS solutions containing 0, 5 µM HPTS and titrated with an acid or base to obtain several pH levels, as measured by a pH-glass electrode. The pH measurements and the fluorescence measurements of the titrated samples were carried out at 37° C. A calibration curve was constructed for both 'open' and 'closed' plate states, allowing pH measurement as a function of the ratio between the two above-mentioned excitation wavelengths.

Type and Preparation of Stimulants

In each test, the metabolic activity profiles of PBMCs were monitored in the basal state (in the absence of stimulant reagents), and under the influence of either a stimulant, a nutrient or an inhibitor (all referred to as 'stimulants') as detailed in Table 3 above. Each stimulant was diluted in buffer working solution to obtain several different concentrations. The selection of stimulants was made by their relation to the immune system, lung cancer or cancers in general.

Data Analysis

All demographic and clinical information, as well as the raw MAP test data, were stored in a secure and dedicated PostgreSQL database. Data analysis was performed using Python.

At the end of the biological analysis, each subject was assigned a data-sheet containing raw fluorescent readings of plate wells as a function of time for both 'open' and 'closed' plate states. The fluorescent readings were transformed into pH values using a calibration curve.

Machine learning was preformed using decision trees, implemented by the scikit-learn Python library. For cross-validation, a stratified k-fold was used. Bagging was executed by training an ensemble of trees on random subsets of the cohort, followed by aggregating their individual predictions using hard voting.

Confidence intervals (CI) were calculated using the normal approximation for the binomial confidence interval. Significance of differences between sub-populations were estimated using the Fisher exact test.

Example 1

Study Design and Demographics

Figure 2:
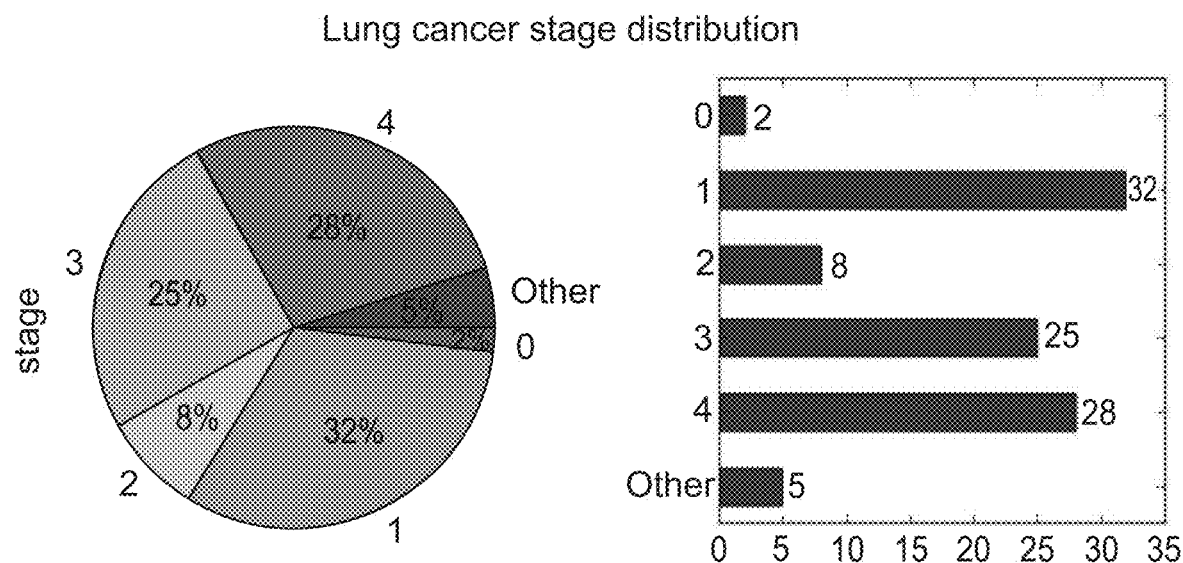
Figure 3:
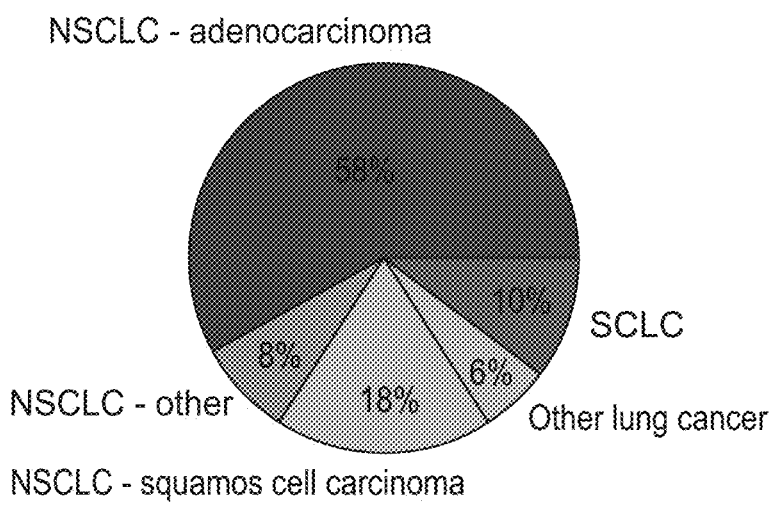

A cohort of 200 subjects was compiled by age- and sex-matching 100 lung cancer subjects with 100 healthy subjects (Table 5, below). The healthy group included both healthy individuals and those diagnosed with COPD, while the lung cancer group included both lung cancer patients and individuals with both lung cancer and COPD. The prevalence of COPD in both groups was similar by design (17% and 21%, respectively), to ensure that the test has no bias towards this condition. As part of the study design, subjects with different stages of lung cancer were included, with emphasis on early stages (FIG. 2). Various histological types of lung cancer were included as well (FIG. 3).

TABLE 5

Breakdown of the resulting cohort. Mean ages are shown with standard deviation and range. The ratio of males to females in each group is presented, as well as the percentage of individuals with COPD.

| | | Age | | | | | |
|---|---|---|---|---|---|---|---|
| | Count | Mean | Std. | Min. | Max. | M/F | COPD |
| Lung cancer | 100 | 65.8 | 10.2 | 34 | 88 | 57/43 | 21% |
| Healthy | 100 | 62.2 | 8.2 | 41 | 83 | 57/43 | 17% |
| All | 200 | 64.0 | 9.4 | 34 | 88 | 114/86 | 19% |

Example 2

Diagnostic Prediction Model Construction

Figure 4:
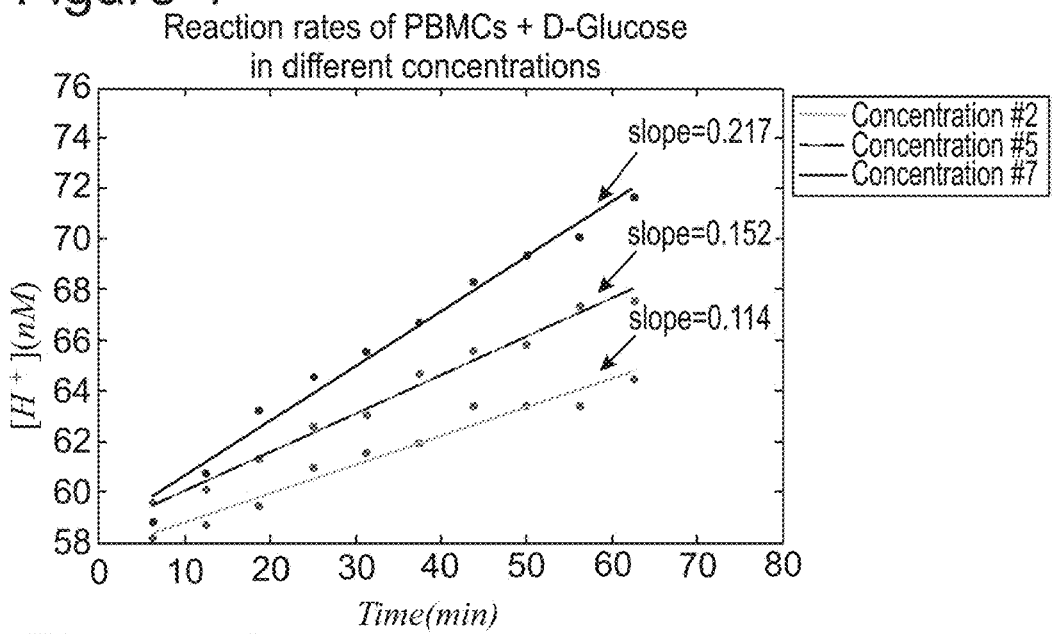
Figure 5A:
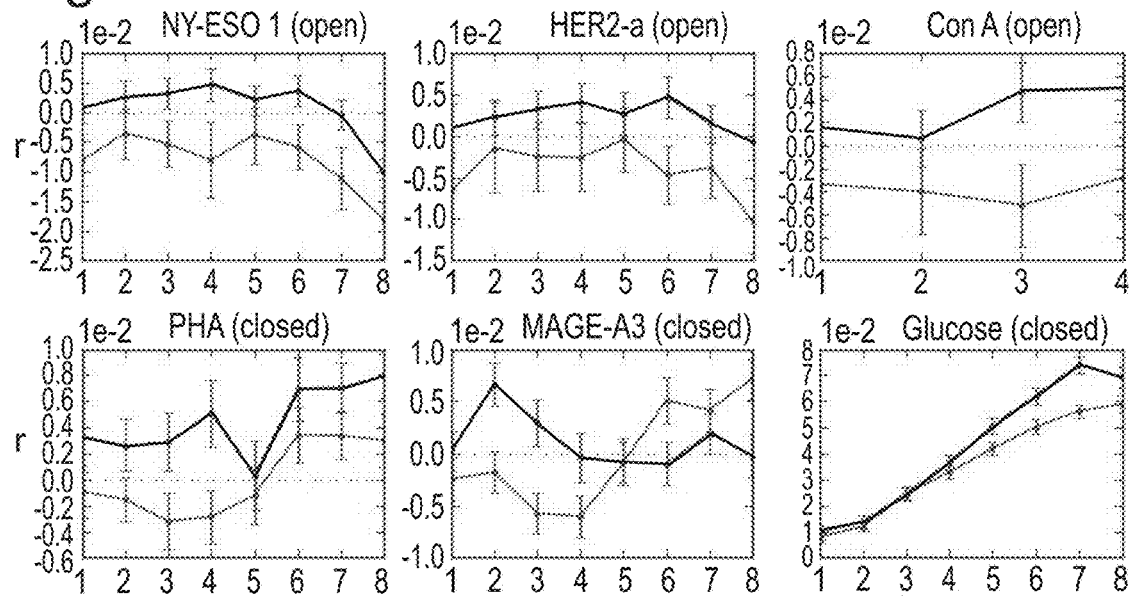
Figure 5B:
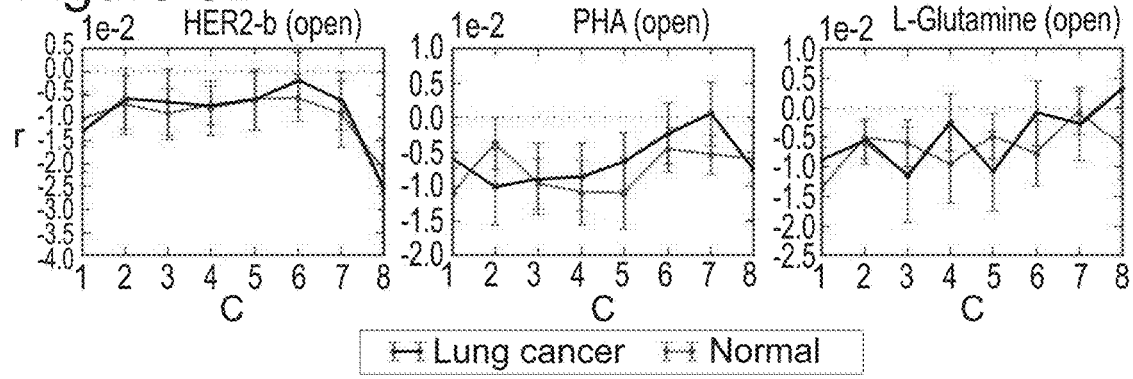

Machine learning methods were utilized to distinguish between lung cancer and healthy subjects. Before this could be done, meaningful features needed to be extracted from the raw data of the MAP test. The data comprise fluorescent reads, representing the acidification levels of the extracellular environment while exposed to varying concentrations of stimulants. It was hypothesized that the presence of cancer, associated with changes in the physiological function of the immune system, will be reflected in different metabolic activity profiles of the tested PBMC samples. Thus, the change in acidity as a function of time, defined as the reaction rate (r), was calculated for the different stimulants and concentrations (FIG. 4). The value of r was then observed as a function of stimulant concentration (C). In many concentrations, a clear-cut difference could be observed between the average values of lung cancer samples and the average of healthy samples (FIGS. 5A-B).

Several mathematical models were used to describe the relationship between C and r, using a small number of coefficients. Some of the models also take into consideration the inter-dependence of different stimulants. To enhance the difference between the two populations with each stimulant, decision tree classifiers were trained to predict the clinical status of subjects ("lung cancer" or "healthy"). The best mathematical model and best classifier parameters were selected for each stimulant, maximizing accuracy, and the final prediction model comprised an ensemble of decision trees, taking into consideration predictions from multiple stimulants. This was coupled with bootstrap aggregation ("bagging") to obtain robust results.

Example 3

Diagnostic Prediction of Lung Cancer and Healthy Subjects

Figure 6:
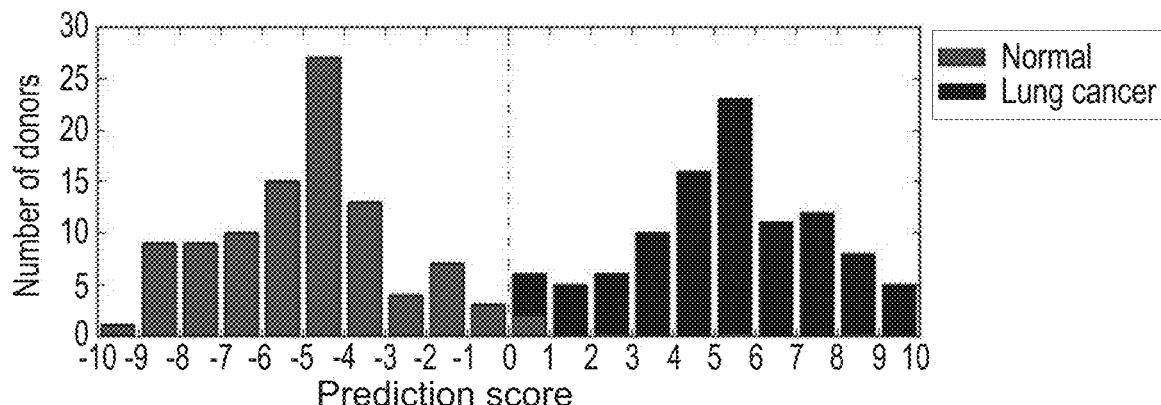
FIG. 6 is a bar graph of prediction scores, showing a separation between populations of healthy and lung cancer subjects. For these results, the prediction model was trained and validated on the entire data set.
Figure 7:
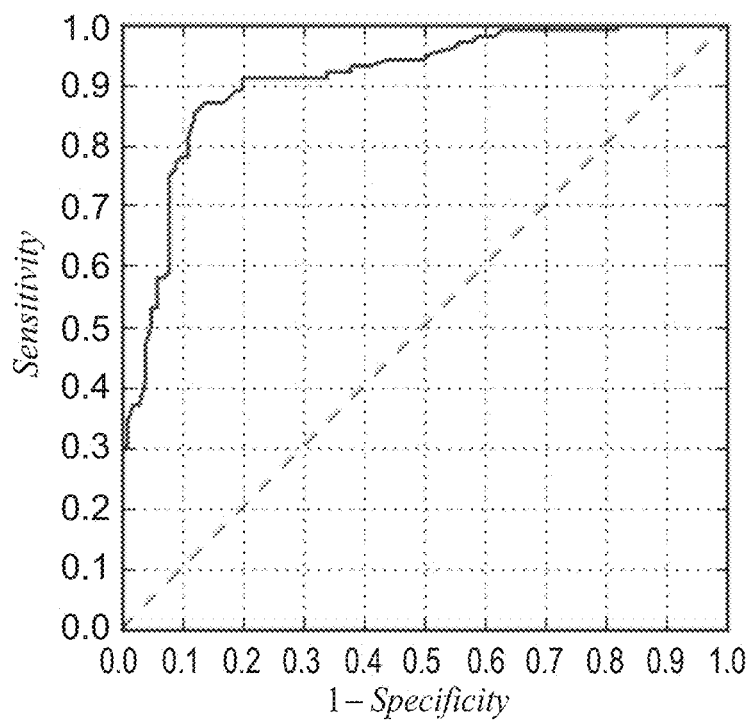
FIG. 7 is a graph showing a ROC curve of the 20-fold cross-validation.

The constructed model produced an almost complete separation between the populations of lung cancer and healthy subjects (FIG. 6), with an apparent performance sensitivity of 100% and specificity of 98%. As a next step, cross-validation (CV) was utilized to test the predictive capability of the model. Specifically, a stratified 20-fold CV analysis was used, in which 10 samples (½₀ of the cohort) are left out for validation, and the rest are used as a training set for the prediction model. The process is repeated iteratively, with a different set of 10 samples each time, until every subject in the cohort is given a prediction. The resulting prediction is a score between −10 (strong healthy) and 10 (strong lung cancer). A receiver operating characteristic (ROC) curve can then be plotted (FIG. 7), and a positivity cut-off (or discrimination threshold) can be set to determine sensitivity and specificity. The obtained area under the curve (AUC) was 0.91, with a sensitivity of 91% and specificity of 80% (95% confidence intervals are [87.7%, 94.3%] and [75.3%, 84.7%], respectively) with the cut-off value set to −0.3 (Table 6, below). Further testing the predictive capabilities of the model, 10-fold and 5-fold CV analyses were performed as well (leaving out 20 and 40 samples respectively each time), resulting in AUCs of 0.91 and 0.86 respectively.

TABLE 6

Performance measures for the 20-fold cross-validation analysis, with the positivity cut-off value set to −0.3.

|  | Result | 95% Confidence interval |
|---|---|---|
| Sensitivity | 91.0% | 87.7%, 94.3% |
| Specificity | 80.0% | 75.3%, 84.7% |
| Positive predictive value (PPV) | 82.0% | 77.5%, 86.5% |
| Negative predictive value (NPV) | 89.9% | 86.4%, 93.4% |
| Accuracy | 85.5% | 81.4%, 89.6% |
| F1 score | 86.3% | 82.3%, 90.3% |

Figure 8:
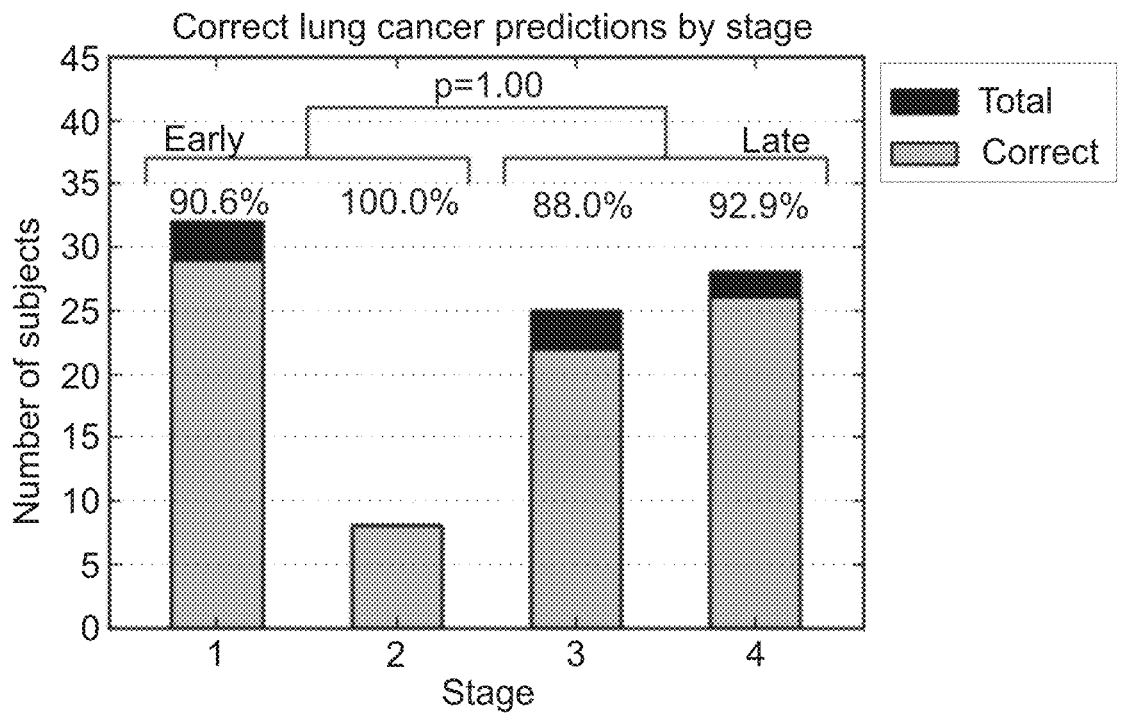
FIG. 8 is a bar graph showing discovery rates of the diagnostic model, broken down into lung cancer stages. P-value of the Fisher exact test is shown.

The prediction model seems to be equally strong in predicting late and early stages of lung cancer. When defining stages 1-2 as early and stages 3-4 as late, there is no observable difference in sensitivity between the two groups (p=1.00). This can be visualized by breaking down the results of the positive group into stages (FIG. 8).

Example 4

Identifying Lung Cancer Over Other Lung Chronic Diseases

Figure 9:
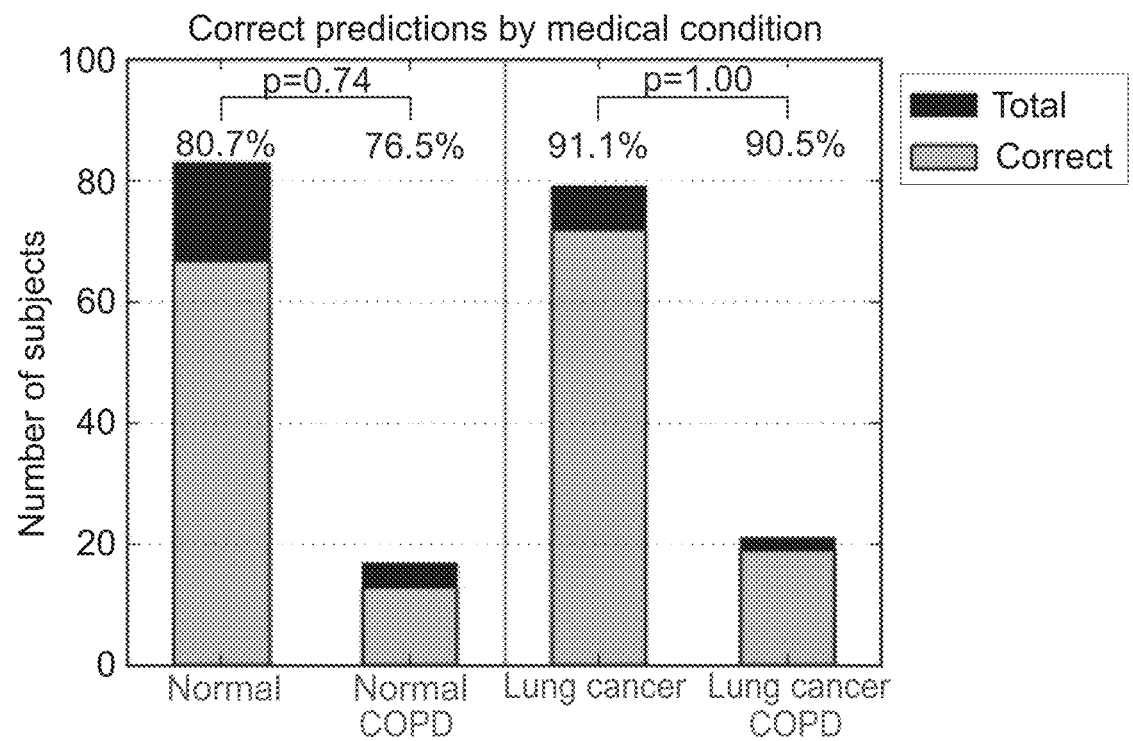
FIG. 9 is a bar graph showing the accuracy of the model, broken down into medical condition groups. P-values of the Fisher exact test are shown.

One important addressed challenge is the ability of embodiments of the map test as described herein to distinguish not only between healthy and lung cancer subjects, but also between those patients with cancer versus other diseases that increase immune system activity. To this end, subjects diagnosed with COPD were included in both the normal and the lung cancer groups in approximately the same ratio. It was observed that the percentage of correct predictions is similar between subjects with and without COPD, in both the healthy group (p=0.74) and the lung cancer group (p=1.00) (FIG. 9). These results suggest that the MAP test's ability to identify lung cancer is not affected by the presence of chronic lung comorbidities.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Example 5

Comparison Between Smoking and Non-Smoking Subpopulations

Since smoking habits have a major influence on the development of lung cancer, it is important to verify the integrity of the prediction model in regard to this variable. The percentage of correct predictions was compared between subjects labeled as smokers (either former or current) and non-smokers. As shown in FIG. 10, there was no significant difference in success rates in both the control group (p=0.32) and the lung cancer group (p=0.68) (FIG. 10). These results suggest that the MAP test's ability to identify lung cancer is not affected by the smoking habits of tested subjects.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of diagnosing lung cancer in a subject-in-need thereof, the method comprising:
   (a) providing a biological sample of the subject which comprises peripheral blood mononuclear cells (PBMCs);
   (b) in vitro contacting said PBMCs with at least one stimulant comprising gastrin releasing peptide (GRP); and
   (c) measuring metabolic activity of said PBMCs having been contacted according to (b), wherein a statistically significant change in said metabolic activity of said PBMCs as compared to a control sample is indicative of lung cancer, wherein said measuring metabolic activity is by measuring extracellular acidification of said PBMCs, and said measuring said metabolic activity is in a time-dependent manner as a function of a concentration of said at least one stimulant so as to generate an acidification profile, wherein said acidification profile is due to secretion of:
   (i) non-volatile soluble metabolic products and volatile soluble metabolic products;
   (ii) non-volatile soluble metabolic products; or
   (iii) volatile soluble metabolic products,
   and wherein said measuring said acidification profile of said (ii) is performed in an air-exposed chamber, and wherein measuring acidification profile of said (i) is performed in an air-sealed chamber, and wherein measuring acidification profile of said (iii) is by subtracting an acidification profile of said (ii) from an acidification profile of said (i).

2. The method of claim 1, wherein said measuring said extracellular acidification is in an extracellular defined solution having a calibrated buffered capacity of said PBMCs.

3. The method of claim 1, further comprising in vitro contacting said PBMCs with at least one additional stimulant selected from the group consisting of New York esophageal squamous cell carcinoma 1 (NY-ESO-1), Her-2/Neu, Melanoma-associated antigen A3 (MAGE-A3), and carcinoembryonic antigen (CEA).

4. The method of claim 3, wherein said measuring is performed in an air-exposed chamber when said stimulant is NY-ESO-1.

5. The method of claim 3, wherein said measuring is performed in an air-exposed chamber when said stimulant is Her-2/Neu.

6. The method of claim 3, wherein said measuring is performed in an air-exposed chamber when said stimulant is GRP.

7. The method of claim 3, wherein said measuring is performed in an air-sealed chamber when said stimulant is phytohaemagglutinin (PHA).

8. The method of claim 3, wherein said measuring is performed in an air-sealed chamber when said stimulant is MAGE-A3.

9. The method of claim 3, wherein said measuring is performed in an air-sealed chamber when said stimulant is CEA.

10. The method of claim 1, wherein said measuring said extracellular acidification of said PBMCs is with a non-toxic, membrane-impermeant pH probe.

11. The method of claim 1, wherein said control sample is of said biological sample without said stimulant.

12. The method of claim 1, wherein said measuring said metabolic activity is at 37° C.

13. A method of treating lung cancer, the method comprising:
(a) diagnosing a subject as having lung cancer according to claim 1;
(b) treating or selecting treatment for said subject with an anti-lung cancer treatment.

14. A method of monitoring treatment, the method comprising:
(a) treating a subject having lung cancer with an anti-lung cancer treatment;
(b) measuring metabolic activity in PBMCs of the subject by:
in vitro contacting said PBMCs with at least one stimulant comprising GRP; and
measuring metabolic activity of said PBMCs having been contacted according to (b), wherein a shift in the metabolic activity of the PBMCs towards that of a normal healthy cell sample examined under identical conditions is indicative of an efficacious treatment of the disease and wherein said measuring metabolic activity is by measuring extracellular acidification of said PBMCs, and said measuring said metabolic activity is in a time-dependent manner as a function of a concentration of said at least one stimulant so as to generate an acidification profile, wherein said acidification profile is due to secretion of:
(i) non-volatile soluble metabolic products and volatile soluble metabolic products;
(ii) non-volatile soluble metabolic products; or
(iii) volatile soluble metabolic products,
and wherein said measuring said acidification profile of said (ii) is performed in an air-exposed chamber, and wherein measuring acidification profile of said (i) is performed in an air-sealed chamber, and wherein measuring acidification profile of said (iii) is by subtracting an acidification profile of said (ii) from an acidification profile of said (i).

15. The method of claim 14, wherein said anti-lung cancer treatment comprises immunotherapy.

16. The method of claim 1, wherein said subject exhibits clinical signs of lung cancer.

17. The method of claim 1, wherein said subject is at risk of lung cancer.

* * * * *

SEQUENCE LISTING

```
<160> NUMBER OF SEQ ID NOS: 51

<210> SEQ ID NO 1
<211> LENGTH: 26
<212> TYPE: PRT
<213> ORGANISM: Artificial sequence
<220> FEATURE:
<223> OTHER INFORMATION: Synthetic peptide

<400> SEQUENCE: 1

His Gly Arg Thr Gln Asp Glu Asn Pro Val Val His Phe Phe Lys Asn
1               5                   10                  15

Ile Val Thr Pro Arg Thr Pro Pro Ser
            20                  25

<210> SEQ ID NO 2
<211> LENGTH: 21
<212> TYPE: PRT
<213> ORGANISM: Artificial sequence
<220> FEATURE:
<223> OTHER INFORMATION: Synthetic peptide

<400> SEQUENCE: 2

Glu Asn Pro Val Val His Phe Phe Lys Asn Ile Val Thr Pro Arg Thr
1               5                   10                  15

Pro Pro Ser Gln
            20
```

```
<210> SEQ ID NO 3
<211> LENGTH: 27
<212> TYPE: PRT
<213> ORGANISM: Artificial sequence
<220> FEATURE:
<223> OTHER INFORMATION: Synthetic peptide

<400> SEQUENCE: 3

Thr Glu Asn Pro Val Val His Phe Phe Lys Asn Ile Val Thr Pro Arg
1               5                   10                  15

Thr Pro Pro Pro Ser Gln Gly Lys Gly Arg Gly
            20                  25

<210> SEQ ID NO 4
<211> LENGTH: 13
<212> TYPE: PRT
<213> ORGANISM: Artificial sequence
<220> FEATURE:
<223> OTHER INFORMATION: Synthetic peptide

<400> SEQUENCE: 4

Val His Phe Phe Lys Asn Ile Val Thr Pro Arg Thr Pro
1               5                   10

<210> SEQ ID NO 5
<211> LENGTH: 26
<212> TYPE: PRT
<213> ORGANISM: Artificial sequence
<220> FEATURE:
<223> OTHER INFORMATION: Synthetic peptide

<400> SEQUENCE: 5

Asp Glu Asn Pro Val Val His Phe Phe Lys Asn Ile Val Thr Pro Arg
1               5                   10                  15

Thr Pro Pro Pro Ser Gln Gly Lys Gly Arg
            20                  25

<210> SEQ ID NO 6
<211> LENGTH: 21
<212> TYPE: PRT
<213> ORGANISM: Artificial sequence
<220> FEATURE:
<223> OTHER INFORMATION: Synthetic peptide

<400> SEQUENCE: 6

Pro Pro Asp Ser Ser Tyr Leu Ser Gly Ala Asn Leu Asn Leu Ser Cys
1               5                   10                  15

His Ser Ala Ser Asn
            20

<210> SEQ ID NO 7
<211> LENGTH: 9
<212> TYPE: PRT
<213> ORGANISM: Artificial sequence
<220> FEATURE:
<223> OTHER INFORMATION: Synthetic peptide

<400> SEQUENCE: 7

Tyr Leu Ser Gly Ala Asn Leu Asn Leu
1               5

<210> SEQ ID NO 8
<211> LENGTH: 20
<212> TYPE: PRT
```

```
<213> ORGANISM: Artificial sequence
<220> FEATURE:
<223> OTHER INFORMATION: Synthetic peptide

<400> SEQUENCE: 8

Ile Ile Ser Pro Pro Asp Ser Ser Tyr Leu Ser Gly Ala Asn Leu Asn
1               5                   10                  15

Leu Ser Cys His
            20

<210> SEQ ID NO 9
<211> LENGTH: 29
<212> TYPE: PRT
<213> ORGANISM: Artificial sequence
<220> FEATURE:
<223> OTHER INFORMATION: Synthetic peptide

<400> SEQUENCE: 9

Thr Pro Ile Ile Ser Pro Pro Asp Ser Ser Tyr Leu Ser Gly Ala Asn
1               5                   10                  15

Leu Asn Leu Ser Cys His Ser Ala Ser Asn Pro Ser Pro
            20                  25

<210> SEQ ID NO 10
<211> LENGTH: 21
<212> TYPE: PRT
<213> ORGANISM: Artificial sequence
<220> FEATURE:
<223> OTHER INFORMATION: Synthetic peptide

<400> SEQUENCE: 10

Pro Pro Asp Ser Ser Tyr Ser Leu Gly Ala Asn Leu Asn Leu Ser Cys
1               5                   10                  15

His Ser Ala Ser Asn
            20

<210> SEQ ID NO 11
<211> LENGTH: 9
<212> TYPE: PRT
<213> ORGANISM: Artificial sequence
<220> FEATURE:
<223> OTHER INFORMATION: Synthetic peptide

<400> SEQUENCE: 11

Tyr Ser Leu Gly Ala Asn Leu Asn Leu
1               5

<210> SEQ ID NO 12
<211> LENGTH: 20
<212> TYPE: PRT
<213> ORGANISM: Artificial sequence
<220> FEATURE:
<223> OTHER INFORMATION: Synthetic peptide

<400> SEQUENCE: 12

Ile Ile Ser Pro Pro Asp Ser Ser Tyr Ser Leu Gly Ala Asn Leu Asn
1               5                   10                  15

Leu Ser Cys His
            20

<210> SEQ ID NO 13
<211> LENGTH: 29
<212> TYPE: PRT
<213> ORGANISM: Artificial sequence
<220> FEATURE:
```

<223> OTHER INFORMATION: Synthetic peptide

<400> SEQUENCE: 13

Thr Pro Ile Ile Ser Pro Pro Asp Ser Ser Tyr Ser Leu Gly Ala Asn
1               5                   10                  15

Leu Asn Leu Ser Cys His Ser Ala Ser Asn Pro Ser Pro
            20                  25

<210> SEQ ID NO 14
<211> LENGTH: 29
<212> TYPE: PRT
<213> ORGANISM: Artificial sequence
<220> FEATURE:
<223> OTHER INFORMATION: Synthetic peptide

<400> SEQUENCE: 14

Ile Ala Lys Ile Thr Pro Asn Asn Asn Gly Thr Tyr Ala Cys Phe Val
1               5                   10                  15

Ser Asn Leu Ala Thr Gly Arg Asn Asn Ser Ile Val Lys
            20                  25

<210> SEQ ID NO 15
<211> LENGTH: 21
<212> TYPE: PRT
<213> ORGANISM: Artificial sequence
<220> FEATURE:
<223> OTHER INFORMATION: Synthetic peptide

<400> SEQUENCE: 15

Pro Asn Asn Asn Gly Thr Tyr Ala Cys Phe Val Ser Asn Leu Ala Thr
1               5                   10                  15

Gly Arg Asn Asn Ser
            20

<210> SEQ ID NO 16
<211> LENGTH: 20
<212> TYPE: PRT
<213> ORGANISM: Artificial sequence
<220> FEATURE:
<223> OTHER INFORMATION: Synthetic peptide

<400> SEQUENCE: 16

Ile Thr Pro Asn Asn Asn Gly Thr Tyr Ala Cys Phe Val Ser Asn Leu
1               5                   10                  15

Ala Thr Gly Arg
            20

<210> SEQ ID NO 17
<211> LENGTH: 9
<212> TYPE: PRT
<213> ORGANISM: Artificial sequence
<220> FEATURE:
<223> OTHER INFORMATION: Synthetic peptide

<400> SEQUENCE: 17

Thr Tyr Ala Cys Phe Val Ser Asn Leu
1               5

<210> SEQ ID NO 18
<211> LENGTH: 20
<212> TYPE: PRT
<213> ORGANISM: Artificial sequence
<220> FEATURE:
<223> OTHER INFORMATION: Synthetic peptide

```
<400> SEQUENCE: 18

Pro Asp Thr Arg Pro Ala Pro Gly Ser Thr Ala Pro Pro Ala His Gly
1               5                   10                  15

Val Thr Ser Ala
            20

<210> SEQ ID NO 19
<211> LENGTH: 40
<212> TYPE: PRT
<213> ORGANISM: Artificial sequence
<220> FEATURE:
<223> OTHER INFORMATION: Synthetic peptide

<400> SEQUENCE: 19

Ala Pro Pro Ala His Gly Val Thr Ser Ala Pro Asp Thr Arg Pro Ala
1               5                   10                  15

Pro Gly Ser Thr Ala Pro Pro Ala His Gly Val Thr Ser Ala Pro Asp
            20                  25                  30

Thr Arg Pro Ala Pro Gly Ser Thr
            35                  40

<210> SEQ ID NO 20
<211> LENGTH: 30
<212> TYPE: PRT
<213> ORGANISM: Artificial sequence
<220> FEATURE:
<223> OTHER INFORMATION: Synthetic peptide

<400> SEQUENCE: 20

Gly Val Thr Ser Ala Pro Asp Thr Arg Pro Ala Pro Gly Ser Thr Ala
1               5                   10                  15

Pro Pro Ala His Gly Val Thr Ser Ala Pro Asp Thr Arg Pro
            20                  25                  30

<210> SEQ ID NO 21
<211> LENGTH: 35
<212> TYPE: PRT
<213> ORGANISM: Artificial sequence
<220> FEATURE:
<223> OTHER INFORMATION: Synthetic peptide

<400> SEQUENCE: 21

Ala His Gly Val Thr Ser Ala Pro Asp Thr Arg Pro Ala Pro Gly Ser
1               5                   10                  15

Thr Ala Pro Pro Ala His Gly Val Thr Ser Ala Pro Asp Thr Arg Pro
            20                  25                  30

Ala Pro Gly
        35

<210> SEQ ID NO 22
<211> LENGTH: 40
<212> TYPE: PRT
<213> ORGANISM: Artificial sequence
<220> FEATURE:
<223> OTHER INFORMATION: Synthetic peptide

<400> SEQUENCE: 22

Arg Cys Gly Ala Arg Gly Pro Glu Ser Arg Leu Leu Glu Phe Tyr Leu
1               5                   10                  15

Ala Met Pro Phe Ala Thr Pro Met Glu Ala Glu Leu Ala Arg Arg Ser
            20                  25                  30
```

```
Leu Ala Gln Asp Ala Pro Pro Leu
        35                  40

<210> SEQ ID NO 23
<211> LENGTH: 26
<212> TYPE: PRT
<213> ORGANISM: Artificial sequence
<220> FEATURE:
<223> OTHER INFORMATION: Synthetic peptide

<400> SEQUENCE: 23

Ser Arg Leu Leu Glu Phe Tyr Leu Ala Met Pro Phe Ala Thr Pro Met
1               5                   10                  15

Glu Ala Glu Leu Ala Arg Arg Ser Leu Ala
            20                  25

<210> SEQ ID NO 24
<211> LENGTH: 32
<212> TYPE: PRT
<213> ORGANISM: Artificial sequence
<220> FEATURE:
<223> OTHER INFORMATION: Synthetic peptide

<400> SEQUENCE: 24

Gly Pro Glu Ser Arg Leu Leu Glu Phe Tyr Leu Ala Met Pro Phe Ala
1               5                   10                  15

Thr Pro Met Glu Ala Glu Leu Ala Arg Arg Ser Leu Ala Gln Asp Ala
            20                  25                  30

<210> SEQ ID NO 25
<211> LENGTH: 20
<212> TYPE: PRT
<213> ORGANISM: Artificial sequence
<220> FEATURE:
<223> OTHER INFORMATION: Synthetic peptide

<400> SEQUENCE: 25

Leu Leu Glu Phe Tyr Leu Ala Met Pro Phe Ala Thr Pro Met Glu Ala
1               5                   10                  15

Glu Leu Ala Arg
            20

<210> SEQ ID NO 26
<211> LENGTH: 19
<212> TYPE: PRT
<213> ORGANISM: Artificial sequence
<220> FEATURE:
<223> OTHER INFORMATION: Synthetic peptide

<400> SEQUENCE: 26

Gly Ser Asp Pro Ala Cys Tyr Glu Phe Leu Trp Gly Pro Arg Ala Leu
1               5                   10                  15

Val Glu Thr

<210> SEQ ID NO 27
<211> LENGTH: 9
<212> TYPE: PRT
<213> ORGANISM: Artificial sequence
<220> FEATURE:
<223> OTHER INFORMATION: Synthetic peptide

<400> SEQUENCE: 27

Phe Leu Trp Gly Pro Arg Ala Leu Val
1               5
```

<210> SEQ ID NO 28
<211> LENGTH: 17
<212> TYPE: PRT
<213> ORGANISM: Artificial sequence
<220> FEATURE:
<223> OTHER INFORMATION: Synthetic peptide

<400> SEQUENCE: 28

Glu Phe Leu Trp Gly Pro Arg Ala Leu Val Glu Thr Ser Tyr Val Lys
1               5                   10                  15

Val

<210> SEQ ID NO 29
<211> LENGTH: 29
<212> TYPE: PRT
<213> ORGANISM: Artificial sequence
<220> FEATURE:
<223> OTHER INFORMATION: Synthetic peptide

<400> SEQUENCE: 29

Val Pro Gly Ser Asp Pro Ala Cys Tyr Glu Phe Leu Trp Gly Pro Arg
1               5                   10                  15

Ala Leu Val Glu Thr Ser Tyr Val Lys Val Leu His His
            20                  25

<210> SEQ ID NO 30
<211> LENGTH: 33
<212> TYPE: PRT
<213> ORGANISM: Artificial sequence
<220> FEATURE:
<223> OTHER INFORMATION: Synthetic peptide

<400> SEQUENCE: 30

Arg Ala Val Pro Leu Pro Ala Gly Gly Gly Thr Val Leu Thr Lys Met
1               5                   10                  15

Tyr Pro Arg Gly Asn His Trp Ala Val Gly His Leu Met Gly Lys Lys
            20                  25                  30

Ser

<210> SEQ ID NO 31
<211> LENGTH: 36
<212> TYPE: PRT
<213> ORGANISM: Artificial sequence
<220> FEATURE:
<223> OTHER INFORMATION: Synthetic peptide

<400> SEQUENCE: 31

Leu Ala Pro Arg Gly Arg Ala Val Pro Leu Pro Ala Gly Gly Gly Thr
1               5                   10                  15

Val Leu Thr Lys Met Tyr Pro Arg Gly Asn His Trp Ala Val Gly His
            20                  25                  30

Leu Met Gly Lys
        35

<210> SEQ ID NO 32
<211> LENGTH: 27
<212> TYPE: PRT
<213> ORGANISM: Artificial sequence
<220> FEATURE:
<223> OTHER INFORMATION: Synthetic peptide

```
<400> SEQUENCE: 32

Val Pro Leu Pro Ala Gly Gly Gly Thr Val Leu Thr Lys Met Tyr Pro
1               5                   10                  15

Arg Gly Asn His Trp Ala Val Gly His Leu Met
            20                  25

<210> SEQ ID NO 33
<211> LENGTH: 47
<212> TYPE: PRT
<213> ORGANISM: Artificial sequence
<220> FEATURE:
<223> OTHER INFORMATION: Synthetic peptide

<400> SEQUENCE: 33

Val Leu Cys Leu Ala Pro Arg Gly Arg Ala Val Pro Leu Pro Ala Gly
1               5                   10                  15

Gly Gly Thr Val Leu Thr Lys Met Tyr Pro Arg Gly Asn His Trp Ala
                20                  25                  30

Val Gly His Leu Met Gly Lys Lys Ser Thr Gly Glu Ser Ser Ser
            35                  40                  45

<210> SEQ ID NO 34
<211> LENGTH: 14
<212> TYPE: PRT
<213> ORGANISM: Artificial sequence
<220> FEATURE:
<223> OTHER INFORMATION: Synthetic peptide

<400> SEQUENCE: 34

Met Tyr Pro Arg Gly Asn His Trp Ala Val Gly His Leu Met
1               5                   10

<210> SEQ ID NO 35
<211> LENGTH: 27
<212> TYPE: PRT
<213> ORGANISM: Artificial sequence
<220> FEATURE:
<223> OTHER INFORMATION: Synthetic peptide

<400> SEQUENCE: 35

Pro Ala Gly Gly Gly Thr Val Leu Thr Lys Met Tyr Pro Arg Gly Asn
1               5                   10                  15

His Trp Ala Val Gly His Leu Met Gly Lys Lys
            20                  25

<210> SEQ ID NO 36
<211> LENGTH: 39
<212> TYPE: PRT
<213> ORGANISM: Artificial sequence
<220> FEATURE:
<223> OTHER INFORMATION: Synthetic peptide

<400> SEQUENCE: 36

Arg Gly Arg Ala Val Pro Leu Pro Ala Gly Gly Gly Thr Val Leu Thr
1               5                   10                  15

Lys Met Tyr Pro Arg Gly Asn His Trp Ala Val Gly His Leu Met Gly
                20                  25                  30

Lys Lys Ser Thr Gly Glu Ser
            35

<210> SEQ ID NO 37
<211> LENGTH: 29
```

```
<212> TYPE: PRT
<213> ORGANISM: Artificial sequence
<220> FEATURE:
<223> OTHER INFORMATION: Synthetic peptide

<400> SEQUENCE: 37

Gly Gly Thr Val Leu Thr Lys Met Tyr Pro Arg Gly Asn His Trp Ala
1               5                   10                  15
Val Gly His Leu Met Gly Lys Lys Ser Thr Gly Glu Ser
            20                  25

<210> SEQ ID NO 38
<211> LENGTH: 5
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: 5'   palmitoyl group

<400> SEQUENCE: 38

Lys Thr Thr Lys Ser
1               5

<210> SEQ ID NO 39
<211> LENGTH: 24
<212> TYPE: PRT
<213> ORGANISM: Artificial sequence
<220> FEATURE:
<223> OTHER INFORMATION: Synthetic peptide

<400> SEQUENCE: 39

Lys Phe Pro Asp Glu Glu Gly Ala Cys Gln Pro Cys Pro Ile Asn Cys
1               5                   10                  15
Thr His Ser Cys Val Asp Leu Asp
            20

<210> SEQ ID NO 40
<211> LENGTH: 22
<212> TYPE: PRT
<213> ORGANISM: Artificial sequence
<220> FEATURE:
<223> OTHER INFORMATION: Synthetic peptide

<400> SEQUENCE: 40

Gly Ala Cys Gln Pro Cys Pro Ile Asn Cys Thr His Ser Cys Val Asp
1               5                   10                  15
Leu Asp Asp Lys Gly Cys
            20

<210> SEQ ID NO 41
<211> LENGTH: 30
<212> TYPE: PRT
<213> ORGANISM: Artificial sequence
<220> FEATURE:
<223> OTHER INFORMATION: Synthetic peptide

<400> SEQUENCE: 41

Ile Trp Lys Phe Pro Asp Glu Glu Gly Ala Cys Gln Pro Cys Pro Ile
1               5                   10                  15
Asn Cys Thr His Ser Cys Val Asp Leu Asp Asp Lys Gly Cys
            20                  25                  30
```

```
<210> SEQ ID NO 42
<211> LENGTH: 10
<212> TYPE: PRT
<213> ORGANISM: Artificial sequence
<220> FEATURE:
<223> OTHER INFORMATION: Synthetic peptide

<400> SEQUENCE: 42

Cys Gln Pro Cys Pro Ile Asn Cys Thr His
1               5                   10

<210> SEQ ID NO 43
<211> LENGTH: 27
<212> TYPE: PRT
<213> ORGANISM: Artificial sequence
<220> FEATURE:
<223> OTHER INFORMATION: Synthetic peptide

<400> SEQUENCE: 43

Met Ser Trp Arg Gly Arg Ser Thr Tyr Tyr Trp Pro Arg Pro Arg
1               5                   10                  15

Tyr Val Gln Pro Pro Glu Met Ile Gly Pro Met
            20                  25

<210> SEQ ID NO 44
<211> LENGTH: 15
<212> TYPE: PRT
<213> ORGANISM: Artificial sequence
<220> FEATURE:
<223> OTHER INFORMATION: Synthetic peptide

<400> SEQUENCE: 44

Ser Thr Tyr Tyr Trp Pro Arg Pro Arg Arg Tyr Val Gln Pro Pro
1               5                   10                  15

<210> SEQ ID NO 45
<211> LENGTH: 20
<212> TYPE: PRT
<213> ORGANISM: Artificial sequence
<220> FEATURE:
<223> OTHER INFORMATION: Synthetic peptide

<400> SEQUENCE: 45

Gly Arg Ser Thr Tyr Tyr Trp Pro Arg Pro Arg Arg Tyr Val Gln Pro
1               5                   10                  15

Pro Glu Met Ile
            20

<210> SEQ ID NO 46
<211> LENGTH: 9
<212> TYPE: PRT
<213> ORGANISM: Artificial sequence
<220> FEATURE:
<223> OTHER INFORMATION: Synthetic peptide

<400> SEQUENCE: 46

Tyr Tyr Trp Pro Arg Pro Arg Arg Tyr
1               5

<210> SEQ ID NO 47
<211> LENGTH: 8
<212> TYPE: PRT
<213> ORGANISM: Artificial sequence
<220> FEATURE:
<223> OTHER INFORMATION: Synthetic peptide

<400> SEQUENCE: 47
```

```
<210> SEQ ID NO 48
<211> LENGTH: 29
<212> TYPE: PRT
<213> ORGANISM: Artificial sequence
<220> FEATURE:
<223> OTHER INFORMATION: Synthetic peptide

<400> SEQUENCE: 48

Leu Val Arg Asp Lys Ile Thr Gly Gln Ser Leu Gly Tyr Gly Phe Val
1               5                   10                  15

Asn Tyr Ile Asp Pro Lys Asp Ala Glu Lys Ala Ile Asn
            20                  25

<210> SEQ ID NO 49
<211> LENGTH: 16
<212> TYPE: PRT
<213> ORGANISM: Artificial sequence
<220> FEATURE:
<223> OTHER INFORMATION: Synthetic peptide

<400> SEQUENCE: 49

Gly Gln Ser Leu Gly Tyr Gly Phe Val Asn Tyr Ile Asp Pro Lys Asp
1               5                   10                  15

<210> SEQ ID NO 50
<211> LENGTH: 9
<212> TYPE: PRT
<213> ORGANISM: Artificial sequence
<220> FEATURE:
<223> OTHER INFORMATION: Synthetic peptide

<400> SEQUENCE: 50

Leu Gly Tyr Gly Phe Val Asn Tyr Ile
1               5

<210> SEQ ID NO 51
<211> LENGTH: 23
<212> TYPE: PRT
<213> ORGANISM: Artificial sequence
<220> FEATURE:
<223> OTHER INFORMATION: Synthetic peptide

<400> SEQUENCE: 51

Asp Lys Ile Thr Gly Gln Ser Leu Gly Tyr Gly Phe Val Asn Tyr Ile
1               5                   10                  15

Asp Pro Lys Asp Ala Glu Lys
            20
```